United States Patent
Sakata et al.

(10) Patent No.: US 8,034,466 B2
(45) Date of Patent: *Oct. 11, 2011

(54) LIGHT-EMITTING ELEMENT AND LIGHT-EMITTING DEVICE USING THE SAME

(75) Inventors: Junichiro Sakata, Atsugi (JP); Hisao Ikeda, Isehara (JP); Sachiko Kawakami, Isehara (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 837 days.

This patent is subject to a terminal disclaimer.

(21) Appl. No.: 11/791,671
(22) PCT Filed: Dec. 5, 2005
(86) PCT No.: PCT/JP2005/022715
§ 371 (c)(1),
(2), (4) Date: May 25, 2007
(87) PCT Pub. No.: WO2006/062218
PCT Pub. Date: Jun. 15, 2006

(65) Prior Publication Data
US 2008/0122345 A1 May 29, 2008

(30) Foreign Application Priority Data

Dec. 6, 2004 (JP) ................................ 2004-353389
Dec. 6, 2004 (JP) ................................ 2004-353406

(51) Int. Cl.
H01J 1/62 (2006.01)
H01L 51/54 (2006.01)
(52) U.S. Cl. ......... 428/690; 428/917; 313/504; 313/506
(58) Field of Classification Search .................. None
See application file for complete search history.

(56) References Cited

U.S. PATENT DOCUMENTS
6,380,672 B1 4/2002 Yudasaka
(Continued)

FOREIGN PATENT DOCUMENTS
CN 1242854 1/2000
(Continued)

OTHER PUBLICATIONS

Office Action (Application No. 200580041834.6) dated Feb. 13, 2009.
(Continued)

*Primary Examiner* — Dawn L. Garrett
(74) *Attorney, Agent, or Firm* — Eric J. Robinson; Robinson Intellectual Property Law Office, P.C.

(57) ABSTRACT

The present invention provides a light-emitting element that includes a pair of electrodes, and an organic compound that has a glass-transition temperature of 150° C. or more, preferably 160° C. or more and 300° C. or less, and a metal oxide that are provided between the pair of electrodes, or includes a pair of electrodes, and a compound having a spiro ring and a triphenylamine skeleton and a metal oxide that are provided between the pair of electrodes. It is a feature that the compound has a spiro ring and a triphenylamine skeleton is a benzidine derivative represented by a general formula (1) In the formula, $R^1$ is hydrogen or an alkyl group having 1 to 4 carbon atoms.

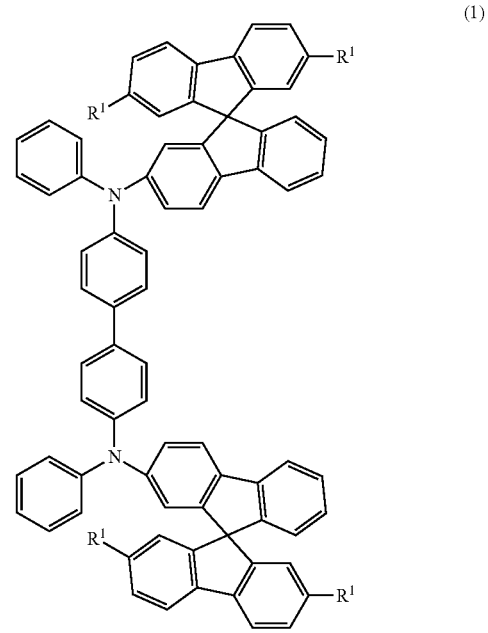

(1)

8 Claims, 21 Drawing Sheets

U.S. PATENT DOCUMENTS

| | | |
|---|---|---|
| 6,416,887 B1 | 7/2002 | Tokito et al. |
| 6,458,476 B1 | 10/2002 | Suzuki et al. |
| 6,642,651 B2 | 11/2003 | Yudasaka |
| 6,885,148 B2 | 4/2005 | Yudasaka |
| 6,916,552 B2 | 7/2005 | Ueda et al. |
| 6,984,462 B2 | 1/2006 | Kim et al. |
| 6,998,487 B2 | 2/2006 | Kim et al. |
| 7,061,009 B2 | 6/2006 | Nelles et al. |
| 7,364,939 B2 | 4/2008 | Yudasaka |
| 7,488,849 B2 * | 2/2009 | Kawakami ............. 564/309 |
| 7,598,667 B2 * | 10/2009 | Kawamura et al. ........ 313/504 |
| 2003/0118866 A1 * | 6/2003 | Oh et al. ............. 428/690 |
| 2003/0189401 A1 | 10/2003 | Kido et al. |
| 2004/0170863 A1 * | 9/2004 | Kim et al. ............ 428/690 |
| 2005/0084712 A1 * | 4/2005 | Kido et al. ........... 428/690 |
| 2006/0049397 A1 * | 3/2006 | Pfeiffer et al. ........... 257/40 |
| 2006/0063027 A1 | 3/2006 | Vestweber et al. |
| 2006/0180812 A1 * | 8/2006 | Sakata et al. ............ 257/40 |
| 2007/0003785 A1 * | 1/2007 | Slusarek et al. ......... 428/690 |
| 2007/0018569 A1 | 1/2007 | Kawamura et al. |
| 2008/0180421 A1 | 7/2008 | Yudasaka |

FOREIGN PATENT DOCUMENTS

| | | |
|---|---|---|
| EP | 0 940 797 | 9/1999 |
| EP | 1 120 840 A2 | 8/2001 |
| EP | 1 120 840 A3 | 8/2001 |
| EP | 1 289 030 | 3/2003 |
| EP | 1 351 558 | 10/2003 |
| EP | 1 505 648 | 2/2005 |
| EP | 1 623 970 | 2/2006 |
| EP | 1 645 552 | 4/2006 |
| EP | 1 294 823 | 12/2006 |
| JP | 09-063771 | 3/1997 |
| JP | 11-273863 | 10/1999 |
| JP | 2001-210474 | 8/2001 |
| JP | 2002-265938 | 9/2002 |
| JP | 2002-313579 | 10/2002 |
| JP | 2002-356449 | 12/2002 |
| JP | 2003-059670 | 2/2003 |
| JP | 2003-197942 | 7/2003 |
| JP | 2003-272860 | 9/2003 |
| JP | 2004-529937 | 9/2004 |
| JP | 2004-339134 | 12/2004 |
| WO | WO 00/27946 | 5/2000 |
| WO | WO 02/088274 | 11/2002 |
| WO | 2004/058911 | 7/2004 |

OTHER PUBLICATIONS

International Search Report (Application No. PCT/JP2005/022715) dated Feb. 7, 2006.

Written Opinion (Application No. PCT/JP2005/022715) dated Feb. 7, 2006.

* cited by examiner

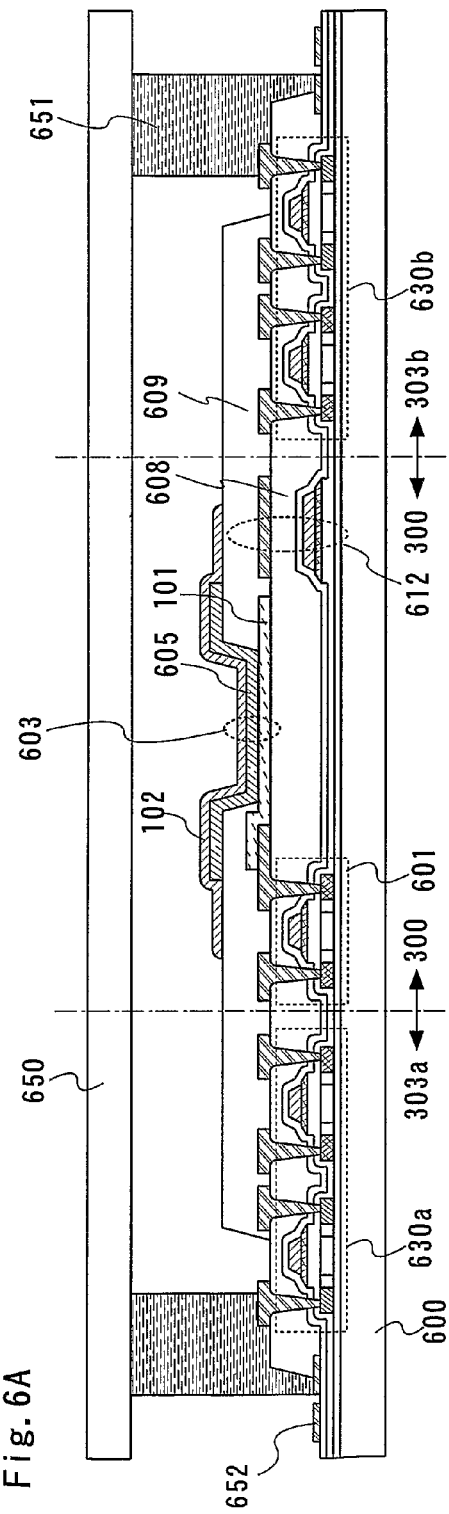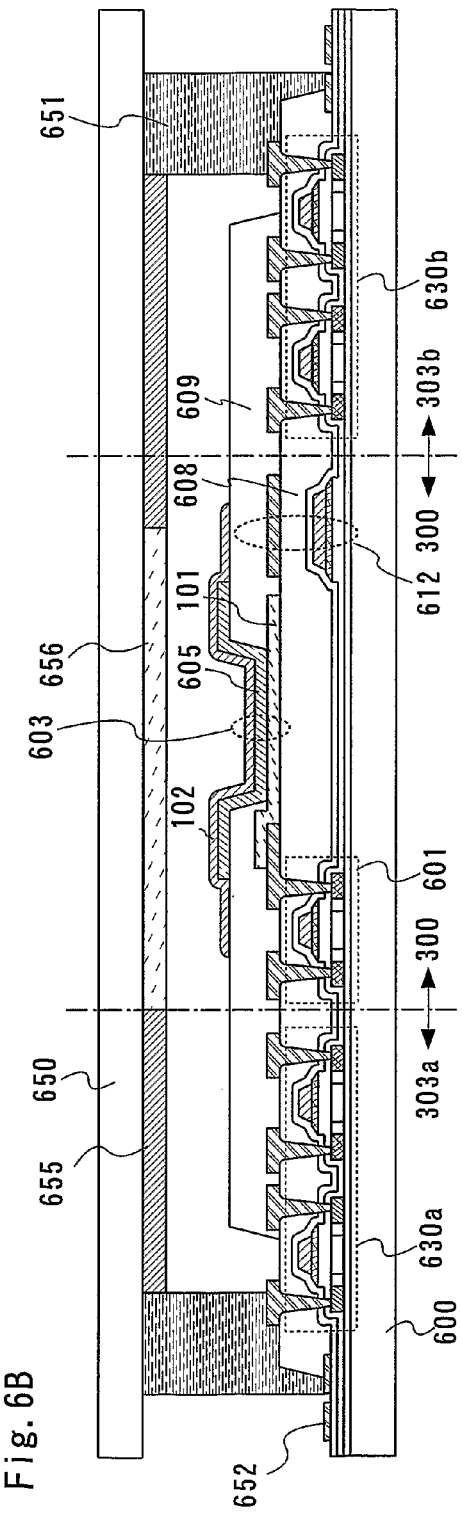
Fig. 6A
Fig. 6B

LIGHT-EMITTING ELEMENT AND LIGHT-EMITTING DEVICE USING THE SAME

TECHNICAL FIELD

The present invention relates to the structure of a light-emitting element including an organic compound and an inorganic compound, and further relates to a light-emitting device that has the light-emitting element.

BACKGROUND ART

Many of light-emitting elements that are used for displays have a structure in which a layer including a luminescent material is sandwiched between a pair of electrodes, and luminescence is produced when an exciton formed by recombining an electron injected from one of the electrodes and a hole injected from the other electrode returns to the ground state.

Regarding these light-emitting elements, studies for improving a luminous efficiency and stability and preventing increase in driving voltage have been conducted.

For example, Patent Document 1 discloses a highly durable organic thin-film light-emitting element that is able to keep light-emitting performance. According to Patent Document 1, it is disclosed that a lower driving voltage for the light-emitting element is achieved by using a metal oxide that has a higher work function, such as a molybdenum oxide, for an anode.

In addition, crystallization of a material constituting a light-emitting element is cited as a cause of deterioration of the light-emitting element. Therefore, a material that is not likely to be crystallized is desired, and for example, Patent Document 2 disclosed a heat-resistant organic material that has a higher glass-transition temperature.

[Patent Reference 1]
   Japanese Patent Application Laid-Open No. 9-63771
[Non-Patent Reference 1]
   WO Publication No. WO00/27946

DISCLOSURE OF INVENTION

This development has been continued since the power consumption of a light-emitting device can be made lower by achieving a lower driving voltage. In particular, when a light-emitting element is incorporated in a mobile light-emitting device, great importance is placed on achievement of lower power consumption.

Therefore, the way disclosed in Patent Document 1 alone is said to be insufficient, and technologic development for achieving a much lower driving voltage has been needed.

Further, for mass production of light-emitting devices, a high-yield structure for a light-emitting element and the production process thereof have been desired.

Consequently, it is an object of the present invention to provide a light-emitting element achieving a lower driving voltage and provide a light-emitting element that can be produced at a high yield. Further, it is an object of the present invention to provide a light-emitting element including a material that has excellent heat resistance, in particular, that is not likely to be crystallized and is likely to be kept amorphous.

Further, it is an object of the present invention to provide a light-emitting device that has this light-emitting element.

In view of the objects described above, the present invention has a feature of a light-emitting element that has a layer including an organic compound that has a glass-transition temperature of 150° C. or more, preferably 160° C. or more and 300° C. or less, and an inorganic compound. In addition, the organic compound according to the present invention has a feature of a melting point that is 180° C. or more and 400° C. or less.

Further, the present invention has a feature of a light-emitting element including an organic compound and an inorganic compound, and has a feature of using a compound having a spiro ring and a triphenylamine skeleton for the organic compound. The inventors have found out that it is preferable to use a benzidine derivative represented by a general formula (1) as the compound having a spiro ring and a triphenylamine skeleton. More specifically, it has been determined that it is preferable to use a benzidine derivative represented by a structure formula (2) as the compound having a spiro ring and a triphenylamine skeleton.

Specific structure according to the present invention will be described below. In addition, a case of using a metal oxide for the inorganic compound will be exemplified.

A light-emitting element according to the present invention includes a pair of electrodes and a plurality of layers provided between the pair of electrodes, where any one of the plurality of layers includes an organic compound that has a glass-transition temperature of 150° C. or more, preferably 160° C. or more and 300° C. or less, and a metal oxide.

The organic compound according to the present invention can be obtained by a coupling reaction of N,N'-diphenylbenzidine with 2-bromo-spiro-9,9'-bifluorene or 2-bromo-2',7'-dialkyl-spiro-9,9'-bifluorene.

In addition, the organic compound according to the present invention can be obtained by a coupling reaction of N,N'-diphenylbenzidine with 2-bromo-spiro-9,9'-bifluorene.

In addition, the present invention has a feature that a layer including the organic compound that has a glass-transition temperature of 150° C. or more, preferably 160° C. or more and 300° C. or less, and the inorganic compound is used as a layer that generates holes. Further, the light-emitting element according to the present invention can include the organic compound that has a glass-transition temperature of 150° C. or more, preferably 160° C. or more and 300° C. or less, as a hole transporting material.

In addition, the present invention has a feature that the organic compound has a melting point of 180° C. or more and 400° C. or less.

Besides, the organic compound is a compound having a spiro ring and a triphenylamine skeleton in the present invention, and a light-emitting element according to the present invention includes a pair of electrodes, and a compound having a spiro ring and a triphenylamine skeleton and a metal oxide that are provided between the pair of electrodes. This organic compound has a melting point of 180° C. or more and 400° C. or less, and has a glass-transition temperature of 90° C. or more, preferably 150° C. or more, more preferably 160° C. or more and 300° C. or less.

In the present invention, it is a feature that the organic compound is a benzidine derivative represented by the general formula (1). Furthermore, a light-emitting element according to the present invention includes a pair of electrodes, and a benzidine derivative represented by the general formula (1) and a metal oxide that are provided between the pair of electrodes.

(1)

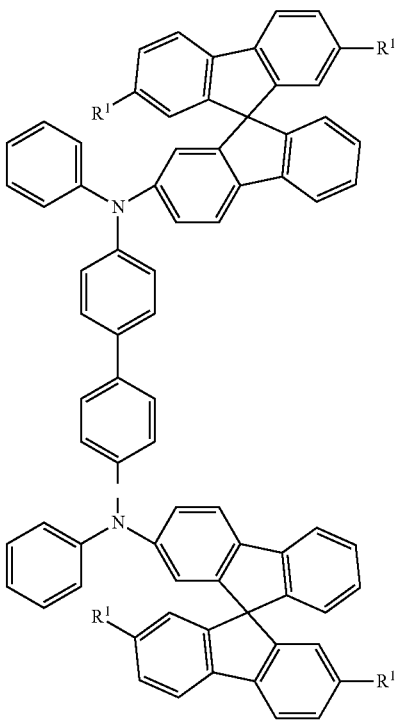

(In the Formula, $R^1$ is Hydrogen or an Alkyl Group Having 1 to 4 Carbon Atoms.)

In the present invention, it is a feature that the organic compound is a benzidine derivative represented by the structure formula (2). Furthermore, a light-emitting element according to the present invention includes a pair of electrodes, and a benzidine derivative represented by the structure formula (2) and a metal oxide that are provided between the pair of electrodes. The benzidine derivative according to the present invention has a glass-transition temperature that meets 150° C. or more, preferably 160° C. or more and 300° C. or less. It is a feature that this benzidine derivative is used as a hole transporting material.

(2)

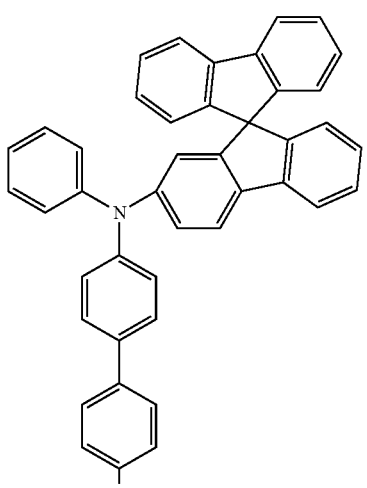

-continued

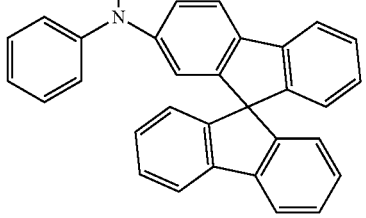

In the present embodiment, a material that is used for the inorganic compound may be a metal nitride or a metal oxynitride besides a metal oxide.

For example, when the inorganic compound described above is used for a layer that functions as an electron accepting material, an oxide of a transition metal belonging to any one of Group 4 to 12 of the periodic table can be used as a specific material. Among others, an oxide of a transition metal belonging to any one of Groups 4 to 8 of the periodic table often has a higher electron accepting property, and a vanadium oxide, a molybdenum oxide, a niobium oxide, a rhenium oxide, a tungsten oxide, a ruthenium oxide, a titanium oxide, a chromium oxide, a zirconium oxide, a hafnium oxide, and a tantalum oxide are particularly preferable.

When the inorganic compound described above is used for a layer that functions as an electron donating material, a metal that is used for the inorganic compound is a material selected from alkali metals and alkali-earth metals, specifically such as lithium (Li), calcium (Ca), sodium (Na), potassium (K), and magnesium (Mg). Specific inorganic compounds include oxides of the alkali metals, oxides of the alkali-earth metals, nitrides of the alkali metals, and nitrides of the alkali-earth metals, specifically, a lithium oxide ($Li_2O$), a calcium oxide (CaO), a sodium oxide ($Na_2O$), a potassium oxide ($K_2O$), and a magnesium oxide (MgO), and further include lithium fluoride (LiF), cesium fluoride (CsF), and calcium fluoride ($CaF_2$).

It is to be noted that "including the organic compound and the inorganic compound" includes a layer in which the organic compound and the inorganic compound are mixed and a layer in which the organic compound and the inorganic compound are laminated in the present invention.

Further, the present invention has a feature of a light-emitting device that has the light-emitting element described above. A specific light-emitting device according to the present invention includes a semiconductor film including an impurity region, a first electrode connected to the impurity region, a second electrode provided to be opposed to the first electrode, and a first layer, a second layer, and a third layer provided in order between the first electrode and the second electrode, where any one of the first to third layers includes an organic compound that has a glass-transition temperature of 150° C. or more, preferably 160° C. or more and 300° C. or less, and a metal oxide. In addition, another light-emitting device according to the present invention includes a semiconductor film including an impurity region, a first electrode connected to the impurity region, a second electrode provided to be opposed to the first electrode, and a first layer, a second layer, and a third layer provided in order between the first electrode and the second electrode, where any one of the first to third layers includes a compound having a spiro ring and a triphenylamine skeleton and a metal oxide.

According to the present invention, a light-emitting element that is not likely to be crystallized can be obtained and a light-emitting element achieving a lower driving voltage can be obtained. In addition, even when the light-emitting element according to the present invention is made thicker, the driving voltage is not increased. Accordingly, the light-emitting element can be formed to be thicker, and can be thus produced at a favorable yield. Further, an electrode and a light-emitting layer can be kept further away from each other depending on which layer is made thicker, and quenching of luminescence can be thus prevented.

Further, the light-emitting element according to the present invention has high thermal stability and high heat resistance, which is preferable. Accordingly, the light-emitting element is less deteriorated with time.

BRIEF DESCRIPTION OF DRAWINGS

In the accompanying drawings:

FIGS. 6A and 6B are cross-sectional views illustrating panels according to the present invention;

BEST MODE FOR CARRYING OUT THE INVENTION

Figure 1:
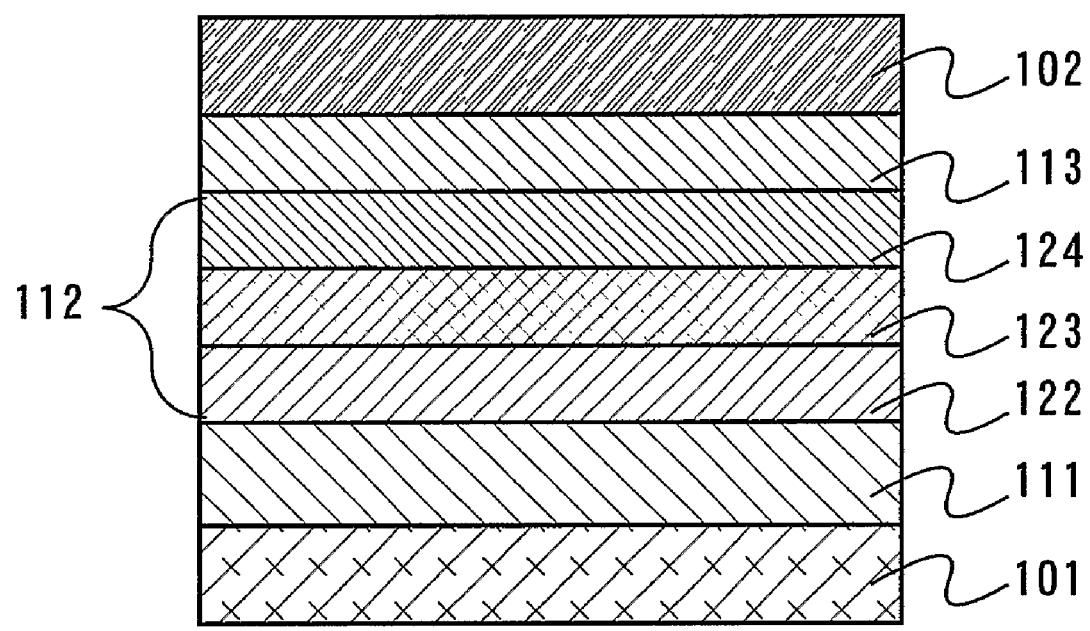
FIG. 1 is a diagram illustrating a light-emitting element according to the present invention.

Embodiments of the present invention will be described below with reference to the accompanying drawings. However, the present invention may be embodied in a lot of different forms, and it is to be easily understood that various changes and modifications will be apparent to those skilled in the art unless such changes and modifications depart from the scope of the present invention. Therefore, the present invention is not to be construed with limitation to what is described in the embodiments. It is to be noted that the same reference numeral denotes the same portion or a portion that has the same function in the all drawings for describing the embodiments, and repeated description of the portion will be omitted.

Embodiment 1

In the present embodiment, an example of a light-emitting element using a layer including an inorganic compound and an organic compound that has a glass-transition temperature of 150° C. or more, preferably 160° C. or more and 300° C. or less, will be described with reference to FIG. 1, where a benzidine derivative is used as the organic compound. It is to be noted that benzidine derivative according to the present invention is a compound having a spiro ring and a triphenylamine skeleton.

As shown in FIG. 1, the light-emitting element according to the present invention has a first electrode 101 and a second electrode 102 that are opposed to each other, and has a first layer 111, a second layer 112, and a third layer 113 that are stacked in this order from the first electrode 101 side. When a voltage is applied to this light-emitting element so that the potential of the first electrode 101 is higher than the potential of the second electrode 102, a hole is injected from the first layer 111 into the second layer 112, and an electron is injected from the third layer 113 into the second layer 112. The hole and the electron are recombined to excite a luminescent material. Then, luminescence is produced when the excited luminescent material returns to the ground state.

Next, the first to third layers 111 to 113, the first electrode 101, and the second electrode 102 will be described.

The first layer 111 is a layer that generates holes. This function can be achieved by using, for example, a layer including a hole transporting material and a material that exhibits an electron accepting property to the hole transporting material. In addition, it is preferable that the material that exhibits an electron accepting property to the hole transporting material be included so that the molar ratio of the material to the hole transporting material is 0.5 to 2 (=the material that exhibits an electron accepting property to the hole transporting material/the hole transporting material).

The hole transporting material is a material in which electrons are transported more then electrodes, and for example, organic compounds, aromatic amine compounds such as 4,4'-bis[N-(1-naphthyl)-N-phenylamino]biphenyl (abbreviation: α-NPD), 4,4'-bis[N-(3-methylphenyl)-N-phenylamino]biphenyl (abbreviation: TPD), 4,4',4"-tris(N,N-diphenylamino)triphenylamine (abbreviation: TDATA), 4, 4',4"-tris [N-(3-methylphenyl)-N-phenylamino]-triphenylamine (abbreviation: MTDATA), 4,4'-bis[N-{4-(N,N-di-m-tolylamino)phenyl}-N-phenylamino]biphenyl (abbreviation:

DNTPD), and phthalocyanine compounds such as phthalocyanine (abbreviation: $H_2Pc$) and copper phthalocyanine (abbreviation: CuPc), can be used as the hole transporting material. It is to be noted that the hole transporting material is not to be considered limited to these.

In addition, an oxide of a transition metal belonging to any one of Group 4 to 12 of the periodic table can be used as the material that exhibits an electron accepting property to the hole transporting material. Among others, an oxide of a transition metal belonging to any one of Groups 4 to 8 of the periodic table often has a higher electron accepting property, and a vanadium oxide, a molybdenum oxide, a niobium oxide, a rhenium oxide, a tungsten oxide, a ruthenium oxide, a titanium oxide, a chromium oxide, a zirconium oxide, a hafnium oxide, and a tantalum oxide are particularly preferable. Besides the oxides, nitrides and oxynitrides of the metals mentioned above may be used. It is to be noted that the material that exhibits am electron accepting property to the hole transporting material is not to be considered limited to these.

When the first layer 111 is formed by using a layer in which the hole transporting material, which is composed of an organic material, and the material that exhibits an electron accepting property to the hole transporting material, which is composed of the inorganic material mentioned above, are mixed, the conductivity thereof gets higher. Therefore, it is preferable to form the first layer 111 in this way. When the conductivity is higher, the first layer 111 can be made thicker, and the yield of manufacturing can be thus improved. Further, the first electrode 101 and the second layer 112 can be kept further away from each other by making the first layer 111 thicker. Accordingly, quenching of luminescence due to a metal can be prevented.

Crystallization of the organic compound that is used for the first layer 111 can be suppressed by using this layer in which the organic material and the inorganic material are mixed, and the first layer 111 can be thus formed to be thicker without increase in resistance. Therefore, even when there is irregularity due to dust, contamination, and the like on a substrate, the irregularity has almost no influence since the first layer 111 is made thicker. Accordingly, defects such as a short circuit between the first electrode 101 and the second electrode 102 due to irregularity can be prevented.

As will be described in further detail below in the example, it is determined that the first layer 111 is not likely to be deteriorated with time when a layer in which a benzidine derivative that has a glass-transition temperature of 150° C. or more, preferably 160° C. or more and 300° C. or less, and a molybdenum oxide that is an inorganic compound are mixed is used for the first layer 111. In short, this structure makes it possible to provide a light-emitting element that is excellent in stability.

Further, the first layer 111 may include another organic compound. As the organic compound, rubrene and the like can be cited. The reliability can be improved by the addition of rubrene.

In addition to this, the first layer 111 may be a layer composed of a metal oxide such as a molybdenum oxide, a vanadium oxide, a ruthenium oxide, a cobalt oxide, and a copper oxide.

This first layer 111 can be formed by evaporation. When a layer including a plurality of mixed compounds is used as the first layer 111, co-evaporation can be used. The co-evaporation includes co-evaporation by resistance-heating evaporation, co-evaporation by electron-beam evaporation, and co-evaporation by resistance-heating evaporation and electron-beam evaporation, and in addition, there are methods such as deposition by resistance-heating evaporation and sputtering and deposition by electron-beam, evaporation and sputtering. The first layer 111 can be formed by combining the same type of methods or different types of methods. In addition, the example described above shows a layer including two kinds of materials. However, when three or more kinds of materials are included, the first layer 111 can be formed also in the same way by combining the same type of methods or different types of methods as described above.

Next, the second layer 112 that is a layer including a light-emitting layer will be described. The layer including the light-emitting layer may be a single layer composed of only the light-emitting layer or a multilayer. To cite a case, a specific multilayer includes a light-emitting layer and additionally a plurality of layers selected from electron transporting layers and hole transporting layers. In FIG. 1, a multilayer case in which the second layer 112 includes a light-emitting layer 123, an electron transporting layer 124, and a hole transporting layer 122 is shown.

A benzidine derivative that has a glass-transition temperature of 150° C. or more, preferably 160° C. or more and 300° C. or less, according to the present invention, which is represented by a general formula (1) or any one of structure formulas (2) to (4), can be used for the hole transporting layer 112.

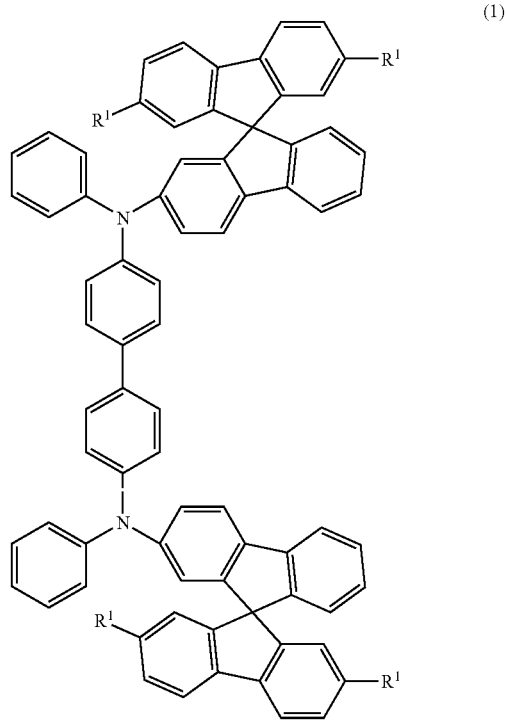

(1)

(2)

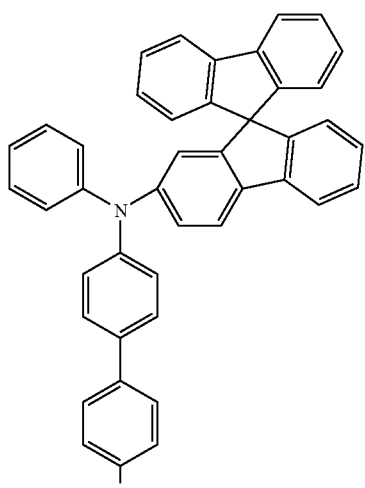

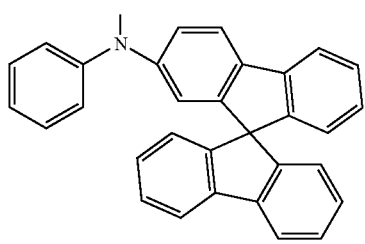

(3)

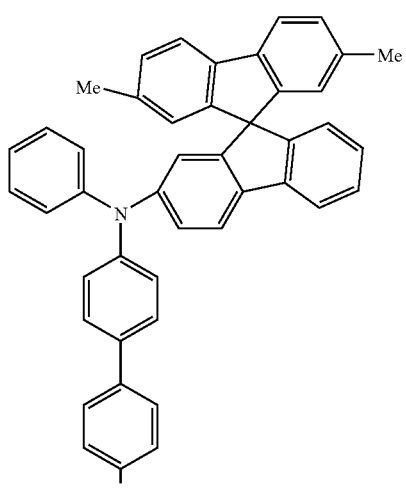

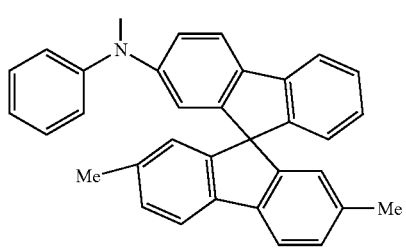

(4)

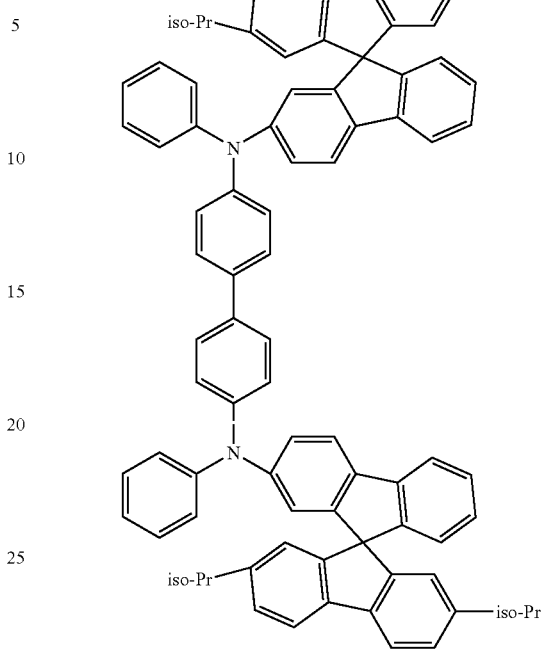

(5)

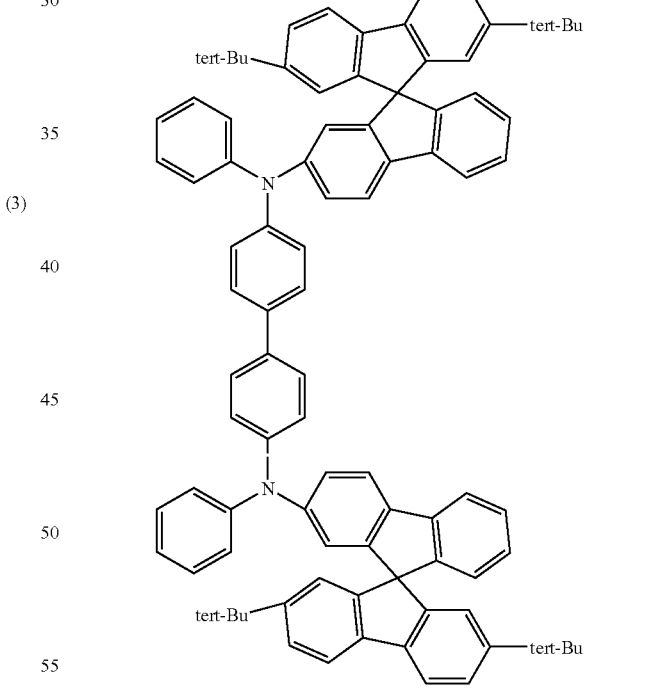

Since the benzidine derivative according to the present invention has high heat resistance, the hole transporting layer 122 that is less likely to change in characteristics due to heat can be formed by using the benzidine derivative according to the present invention as a hole transporting material. Further, since the benzidine derivative according to the present invention is not likely to be crystallized, the hole transporting layer 122 that is not likely to be crystallized can be formed by using the benzidine derivative according to the present invention as a hole transporting material.

It is to be noted that the hole transporting layer 112 may be a layer formed by combining two or more layers each including the benzidine derivative according to the present invention, which is represented by the general formula (1) or any one of the structure formulas (2) to (4).

Further, it is preferable that a layer in which the benzidine derivative that has a glass-transition temperature of 150° C. or more, preferably 160° C. or more and 300° C. or less, according to the present invention, and an inorganic compound are mixed be used for the hole transporting layer 122. Crystallization of the benzidine derivative can be further suppressed by mixing the inorganic compound, and the layer can be thus formed to be thicker without increase in resistance. Therefore, even when there is irregularity due to dust, contamination, and the like, on a substrate, the irregularity has almost no influence due to the hole transporting layer 122 being thicker. Accordingly, defects such as a short circuit between the first electrode 101 and the second electrode 102 due to irregularity can be prevented.

Metal oxides, metal nitrides, and metal oxynitrides can be used for this inorganic compound. For example, an oxide of a transition metal belonging to any one of Group 4 to 12 of the periodic table can be used as a metal oxide. Among others, an oxide of a transition metal belonging to any one of Groups 4 to 8 of the periodic table often has a higher electron accepting property, and a vanadium oxide, a molybdenum oxide, a niobium oxide, a rhenium oxide, a tungsten oxide, a ruthenium oxide, a titanium oxide, a chromium oxide, a zirconium oxide, a hafnium oxide, and a tantalum oxide are particularly preferable.

Next, the light-emitting layer 123 will be described. It is preferable that the light-emitting layer 123 be a layer including a luminescent material dispersed in a material that has a larger energy gap than the luminescent material. However, the light-emitting layer 123 is not to be considered limited to this. It is to be noted that the energy gap indicates the energy gap between the LUMO level and the HOMO level. In addition, a material that provides a favorable luminous efficiency and is capable of producing luminescence of a desired emission wavelength may be used for the luminescent material.

In addition, for the material that is used for dispersing the luminescent material, for example, anthracene derivatives such as anthracene derivatives such as 9,10-di(2-naphthyl)-2-tert-butylanthracene (abbreviation: t-BuDNA), carbazole derivatives such as 4,4'-bis(N-carbazolyl)-biphenyl (abbreviation: CBP), and metal complexes such as bis[2-(2-hydroxyphenyl)-pyridinato]zinc (abbreviation: $Znpp_2$) and bis[2-(2-hydroxyphenyl)-benzoxazolato]zinc (abbreviation: ZnBOX) can be used. However, the material that is used for dispersing the luminescent material is not limited to these materials. When the luminescent material is dispersed as described above, concentration quenching of luminescence from the luminescent material can be prevented.

In order to produce white or whitish light emission from this light-emitting layer 123, for example, a structure of TPD (aromatic diamine), 3-(4-tert-butylphenyl)-4-phenyl-5-(4-biphenylyl)-1,2,4-triazole (abbreviation: TAZ), tris(8-quinolinolato) aluminum (abbreviation: $Alq_3$), $Alq_3$ doped with NileRed that is a red luminescent dye, and $Alq_3$ that are laminated by evaporation or the like in this order from the first electrode 101 side can be used.

In addition, a structure of NPB, NPB doped with perylene, bis(2-methyl-8-quinolinolato)-4-phenylphenolato-aluminum (abbreviation: BAlq) doped with DCM1, BAlq, and $Alq_3$ that are laminated by evaporation or the like in this order from the first electrode 101 side can be used.

In addition, white or whitish light emission can be obtained by dispersing 30 wt % 2-(4-biphenylyl)-5-(4-tert-butylphenyl)-1,3,4-oxadiazole (abbreviation: PBD) as an electron transporting agent in poly(N-vinylcarbasole) (abbreviation: PVK) and dispersing appropriate amounts of four kinds of dyes (TPB, coumarin 6, DCM 1, and NileRed).

Moreover, white or whitish light emission can be also obtained by forming the light-emitting layer 123 using a laminated structure with the use of materials that produce luminescence in relation of complementary colors to each other, for example, a first and second layers using luminescent materials for red and blue-green, respectively.

In the case of emitting white or whitish light as described above, full-color display can be performed with the use of a color filter or a color conversion layer. It is to be noted that mono-color display can be performed in the case of using a monochromatic color filter or a monochromatic color conversion layer.

Further, materials for the light-emitting layer 123 can be appropriately selected besides the light-emitting elements described above, which provide white or whitish light emission. For example, the light-emitting layer 123 may be formed by using respective luminescent materials for red (R), green (G), and blue (B).

For example, when red or reddish luminescence is desired to be obtained, 4-dicyanomethylene-2-isopropyl-6-[2-(1,1,7,7-tetramethyljulolidine-9-yl)ethenyl]-4H-pyran (abbreviation: DCJTI), 4-dicyanomethylene-2-methyl-6-[2-(1,1,7,7-tetramethyljulolidine-9-yl)ethenyl]-4H-pyran (abbreviation: DCJT), 4-dicyanomethylene-2-tert-butyl-6-[2-(1,1,7,7-tetramethyljulolidine-9-yl)ethenyl]-4H-pyran (abbreviation: DCJTB), periflanthene, and 2,5-dicyano-1,4-bis-[2-(10-methoxy-1,1,7,7-tetramethyljulolidine-9-yl)ethenyl]-benzene, bis[2,3-bis(4-fluorophenyl)quinoxalinato]iridium (acetylacetonato) (abbreviation: $Ir(Fdpq)_2(acac)$), and the like can be used for the light-emitting layer 123. However, the material for obtaining red or reddish luminescence is not limited to these materials, and a material that produces luminescence with an emission spectrum peak from 600 nm to 700 nm can be used.

When green or greenish luminescence is desired to be obtained, N,N'-dimethylquinacridone (abbreviation: DMQd), coumarin 6, coumarin 545T, tris(8-quinolinolato) aluminum (abbreviation: $Alq_3$), and the like can be used for the light-emitting layer 123. However, the material for obtaining green or greenish luminescence is not limited to these materials, and a material that produces luminescence with an emission spectrum peak from 500 nm to 600 nm can be used.

In addition, when blue or bluish luminescence is desired to be obtained, 9,10-bis(2-naphthyl)-tert-butylanthracene (abbreviation: t-BuDNA), 9,9'-bianthryl, 9,10-diphenylanthracene (abbreviation: DPA), 9,10-bis(2-naphthyl)anthracene (abbreviation: DNA), bis(2-methyl-8-quinolinolato)-4-phenylphenolato-gallium (abbreviation: BGaq), bis(2-methyl-8-quinolinolato)-4-phenylphenolato-aluminum (abbreviation: BAlq), and the like can be used for the light-emitting layer 123. However, the material for obtaining blue or bluish luminescence is not limited to these materials, and a material that produces luminescence with an emission spectrum peak from 400 nm to 500 nm can be used.

Also, when the light-emitting layer 123 is formed to include respective luminescent materials for red (R), green (G), and blue (B), the peak of each emission spectrum and the like may be adjusted by providing a color filter or a color conversion layer. A color filter or a color conversion layer may be formed on the side from which light emission is extracted outside, or can be provided on any of the substrate side where a thin film transistor is formed and the opposed substrate side.

Next, the electron transporting layer 124 will be described. The electron transporting layer 124 is a layer that has a function of transporting electrons injected from the second electrode 102 to the light-emitting layer 123. By providing the electron transporting layer 124 in this way to keep the second electrode 102 and the light-emitting layer 123 further away from each other, quenching of luminescence due to a metal can be prevented.

It is to be noted that the electron transporting layer 124 is not particularly limited, and can be formed by using a metal complex having a quinoxaline skeleton or a benzoquinoline skeleton, such as tris(8-quinolinolato) aluminum (abbreviation: $Alq_3$), tris(4-methyl-8-quinolinolato) aluminum (abbreviation: $Almq_3$), bis(10-hydroxybenzo[h]-quinolinato) beryllium (abbreviation: $BeBq_2$), and bis(2-methyl-8-quinolinolato)-4-phenylphenolato-aluminum (abbreviation: BAlq). In addition, the electron transporting layer 124 may be formed by using a metal complex having an oxazole-based or thiazole-based ligand, such as bis[2-(2-hydroxyphenyl)-benzoxazolato]zinc (abbreviation: $Zn(BOX)_2$) and bis[2-(2-hydroxyphenyl)-benzothiazolato]zinc (abbreviation: $Zn(BTZ)_2$). Moreover, the electron transporting layer 124 may be formed by using 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or the like.

It is preferable that the electron transporting layer 124 be formed with the use of a material in which the hole mobility is higher than the electron mobility. Further, it is more preferable that the electron transporting layer 124 be formed with the use of a material that has an electron mobility of $10^{-6}$ $cm^2/Vs$ or more. In addition, the electron transporting layer 124 may have a laminated structure formed by combining two or more layers each including the material described above.

Further, it is preferable that a layer in which the organic compound described above and an inorganic compound are mixed is used for the electron transporting layer 124. Crystallization of the organic compound can be further suppressed by mixing the inorganic compound, and the layer can be thus formed to be thicker without increase in resistance. Therefore, even when there is irregularity due to dust, contamination, and the like, on a substrate, the irregularity has almost no influence due to the electron transporting layer 124 being thicker. Accordingly, defects such as a short circuit between the first electrode 101 and the second electrode 102 due to irregularity can be prevented.

Metal oxides, metal nitrides, and metal oxynitrides can be used for this inorganic compound. For example, the metal oxides include a lithium oxide ($Li_2O$), a calcium oxide (CaO), a sodium oxide ($Na_2O$), a potassium oxide ($K_2O$), a magnesium oxide (MgO), and further include a lithium fluoride (LiF), a cesium fluoride (CsF), and calcium fluoride ($CaF_2$).

This second layer 112 can be manufactured by evaporation. When a mixed layer is formed for the second layer 112, co-evaporation can be used. The co-evaporation includes co-evaporation by resistance-heating evaporation, co-evaporation by electron-beam evaporation, and co-evaporation by resistance-heating evaporation and electron-beam evaporation, and in addition, there are methods such as deposition by resistance-heating evaporation and sputtering and deposition by electron-beam evaporation and sputtering. The first layer 111 can be formed by combining the same type of methods or different types of methods. In addition, the example described above shows a layer including two kinds of materials. However, when three or more kinds of materials are included, the first layer 111 can be formed also in the same way by combining the same type of methods or different types of methods as described above.

Next, the third layer 113 that is layer that generates electrons will be described. As this third layer 113, for example, a layer including an electron transporting material and a material that exhibits an electron donating property to the electron transporting material can be cited.

It is to be noted that the electron transporting material is a material in which more electrons are transported than holes, and for example, metal complexes such as tris (8-quinolinolato) aluminum (abbreviation: $Alq_3$), tris(4-methyl-8-quinolinolato) aluminum (abbreviation: $Almq_3$), bis(10-hydroxybenzo[h]-quinolinato)beryllium (abbreviation: $BeBq_2$), bis (2-methyl-8-quinolinolato)-4-phenylphenolato-aluminum (abbreviation: BAlq), bis[2-(2-hydroxyphenyl)-benzoxazolato]zinc (abbreviation: $Zn(BOX)_2$), and bis[2-(2-hydroxyphenyl)-benzothiazolato]zinc (abbreviation: $Zn(BTZ)_2$), and further, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), and 4,4-bis(5-methylbenzoxazol-2-yl)stilbene (abbreviation: BzOs) can be used for the electron transporting material. In addition, the third layer 113 can be formed with the use of an n-type semiconductor. However, the electron transporting material is not limited to these.

In addition, for the material that exhibits an electron donating property to the electron transporting material, a substance selected from alkali metals and alkali-earth metals, specifically such as lithium (Li), calcium (Ca), sodium (Na), potassium (K), and magnesium (Mg), can be used. Further, specific materials include oxides of the alkali metals, oxides of the alkali-earth metals, nitrides of the alkali metals, and nitrides of the alkali-earth metals, specifically, a lithium oxide ($Li_2O$), a calcium oxide (CaO), a sodium oxide ($Na_2O$), a potassium oxide ($K_2O$), and a magnesium oxide (MgO), and further include lithium fluoride (LiF), cesium fluoride (CsF), and calcium fluoride ($CaF_2$). However, the material that exhibits an electron donating property to the electron transporting material is not limited to these. It is to be noted that it is preferable that the material that exhibits an electron donating property to the electron transporting material be included so that the molar ratio of material that exhibits an electron donating property to the electron transporting material to the electron transporting material is 0.5 or more and 2 or less (=the material that exhibits an electron donating property to the electron transporting material/the electron transporting material).

Alternatively, the third layer 113 may be a layer composed of a material such as zinc oxide, zinc sulfide, zinc selenide, tin oxide, or titanium oxide.

The third layer 113 is preferably formed by using a layer in which the above-mentioned organic compound and an inorganic compound are mixed. Accordingly, the conductivity of the third layer 113 can be made higher. When the conductivity is higher, the third layer 113 can be made thicker, and the yield of manufacturing can be thus improved. Further, the light-emitting layer 123 and the second electrode 102 can be kept further away from each other by making the third layer 113 thicker, and quenching of luminescence can be thus prevented.

Further, crystallization of the organic compound that is used for the third layer 113 can be suppressed by using the layer in which the organic material and the inorganic material are mixed, and the third layer 113 can be thus formed to be thicker without increase in resistance. Therefore, even when there is irregularity due to dust, contamination, and the like on a substrate, the irregularity has almost no influence since the first layer 111 is made thicker. Accordingly, defects such as a short circuit between the first electrode 101 and the second electrode 102 due to irregularity can be prevented.

This third layer 113 can be manufactured by evaporation. When a mixed layer is formed for the third layer 113, co-evaporation can be used. The co-evaporation includes co-evaporation by resistance-heating evaporation, co-evaporation by electron-beam evaporation, and co-evaporation by resistance-heating evaporation and electronic-beam evaporation, and in addition, there are methods such as deposition by resistance-heating evaporation and sputtering and deposition by electron-beam evaporation and sputtering. The first layer 111 can be formed by combining the same type of methods or different types of methods. In addition, the example described above shows a layer including two kinds of materials. However, when three or more kinds of materials are included, the first layer 111 can be formed also in the same way by combining the same type of methods or different types of methods as described above.

In the light-emitting element described above, the difference between the electron affinity of the electron transporting material included in the third layer 113 and the electron affinity of the material included in the layer in contact with the third layer 113 among the layers included in the second layer 112 is preferably 2 eV or less, more preferably 1.5 eV or less. Alternatively, when the third layer 113 is composed of an n-type semiconductor, the difference between the work function of the n-type semiconductor and the electron affinity of the material included in the layer in contact with the third layer 113 among the layers included in the second layer 112 is preferably 2 eV or less, more preferably 1.5 eV or less. By joining the second layer 112 and the third layer 113 as described above, electrons can be injected more easily from the third layer 113 to the second layer 112.

It is to be noted that the present invention has a feature of a light-emitting element including an organic compound as typified by an organic compound a benzidine derivative that has a glass-transition temperature of 150° C. or more, preferably 160° C. or more and 300° C. or less and an inorganic compound between a pair of electrodes, and is not to be considered limited to the structure of the light-emitting element shown in FIG. 1. For example, there may be a case where the electron transporting layer 124 is not provided although the structure provided with the electron transporting layer 124 formed in contact with the third layer 113 is shown. Accordingly, the light-emitting layer 123 in contact with the third layer 113 is provided. In this case, a material for dispersing a luminescent material is preferably used for the light-emitting layer 123. Also, it may well be that the electron transporting layer 124 is not provided.

In addition, a material that is capable of producing luminescence without being dispersed, such as $Alq_3$, can be used for the light-emitting layer 123. Since the material such as $Alq_3$ is a luminescent material that has a favorable carrier transporting property, a layer composed of only $Alq_3$ can function as a light-emitting layer without dispersing $Alq_3$. In this case, the light-emitting layer 123 corresponds to a luminescent material itself.

These first to third layers 111 to 113 can be formed by the same method, and can be therefore formed continuously without being exposed to the air. Impurity mixing into an interface and the like can be reduced by forming the first to third layers 111 to 113 continuously without being exposed to the air in this way.

Next, the electrodes will be described. Each of the first electrode 101 and the second electrode 102 are formed by using a conductive material. Further, the electrode provided on the side from which light from the light-emitting layer is extracted outside needs to have a light-transmitting property in addition to conductivity. The light-transmitting property can be obtained also by forming a quite thin film composed of a material that has no light-transmitting property.

As a material for the first electrode 101, light-transmitting materials such as indium tin oxide (ITO), indium tin oxide containing silicon oxide (hereinafter, referred to as ITSO), and indium oxide containing zinc oxide, and in addition, metal materials such as gold (Au), platinum (Pt), nickel (Ni), tungsten (W), chromium (Cr), molybdenum (Mo), iron (Fe), cobalt (Co), copper (Cu), and palladium (Pd) can be used in addition to aluminum (Al). Further, the first electrode 101 can be formed, for example, by sputtering or evaporation. However, the material for the first electrode 101 is not limited to these.

When the above-mentioned material that has no light-transmitting property is used and the first electrode 101 needs to have a light-transmitting property, a thin film composed of the material may be formed.

In addition, a single-layer of the metal material mentioned above or a lamination layer can be used for the first electrode 101. Therefore, when a lamination layer is used for the first electrode 101, it is also possible to use a structure of forming a thin film of the material mentioned above and laminating a light-transmitting material thereon. Of course, the first electrode 101 may be formed with the use of the thin material as a single layer. In order to prevent the resistance from increasing by forming the first electrode 101 to be thin, an auxiliary wiring can also be provided. Further, the use of a lamination layer can prevent the resistance from increasing.

Further, as a material for the second electrode 102, light-transmitting materials such as indium tin oxide (ITO), indium tin oxide containing silicon oxide (ITSO), and indium oxide containing zinc oxide, and metal materials such as gold (Au), platinum (Pt), nickel (Ni), tungsten (W), chromium (Cr), molybdenum (Mo), iron (Fe), cobalt (Co), copper (Cu), and palladium (Pd) can be used. However, the material for the first electrode 101 is not limited to these.

When the above-mentioned material that has no light-transmitting property is used and the second electrode 102 needs to have a light-transmitting property, a thin film composed of the material may be formed.

In addition, a single layer of the metal material mentioned above or a lamination layer can be used for the second electrode 102. Therefore, when a lamination layer is used for the second electrode 102, it is also possible to use a structure of forming a thin film of the material mentioned above and laminating a light-transmitting material thereon. Of course, the second electrode 102 may be formed with the use of the thin material as a single layer. In order to prevent the resistance from increasing by forming the second electrode 102 to be thin, an auxiliary wiring can also be provided. Further, the use of a lamination layer can prevent the resistance from increasing.

It is to be noted that the first electrode 101 or the second electrode 103 can be an anode or a cathode depending on a voltage that is applied to the light-emitting element. In the case of an anode, a material that has a larger work function (a work function of 4.0 eV or more) is used. Alternatively, in the case of a cathode, a material that has a smaller work function (a work function of 3.8 eV or less) is used.

The first electrode 101 or the second electrode 102 can be formed by sputtering, evaporation, or the like. In the case of using evaporation, the first electrode 101, the first to third layers 111 to 113, and the second electrode 102 can be formed continuously without being exposed to the air. Impurity mixing into an interface and the like can be reduced by forming the light-emitting element continuously without being exposed to the air in this way.

As described above, according to the present invention, a light-emitting element that is less likely to change in characteristics by change in characteristics of a hole transporting layer due to heat can be obtained by forming a layer that generates holes with the use of a layer including an organic compound as typified by a benzidine derivative that has a glass-transition temperature of 150° C. or more, preferably 160° C. or more and 300° C. or less and an inorganic compound.

Further, by forming a layer that generates holes with the use of a layer including an organic compound as typified by a benzidine derivative that has a glass-transition temperature of 150° C. or more, preferably 160° C. or more and 300° C. or less and an inorganic compound, a light-emitting element that is less likely to be deteriorated by crystallization of the layer can be obtained.

Accordingly, a light-emitting element achieving a lower driving voltage can be obtained. Further, even when the light-emitting element according to the present invention is made thicker, the driving voltage is not increased. Accordingly, the light-emitting element can be formed to be thicker, and can be thus produced at a favorable yield. Further, a light-emitting layer can be kept further away from a first electrode or a second electrode by making a layer thicker, and quenching of luminescence can be thus prevented.

As described above, the present embodiment is described with the use of a benzidine derivative as an organic compound that has a glass-transition temperature of 150° C. or more, preferably 160° C. or more and 300° C. or less. However, the present invention provides a light-emitting element that includes a layer in which an organic compound and a metal oxide are mixed, and is not limited to the present embodiment as long as an effect of reduced deterioration with time is achieved.

Embodiment 2

An example of a light-emitting element using a layer including a benzidine derivative according to the present invention, which is a compound having a spiro ring and a triphenylamine skeleton, and an inorganic compound will be described with reference to FIG. 18.

Figure 18:
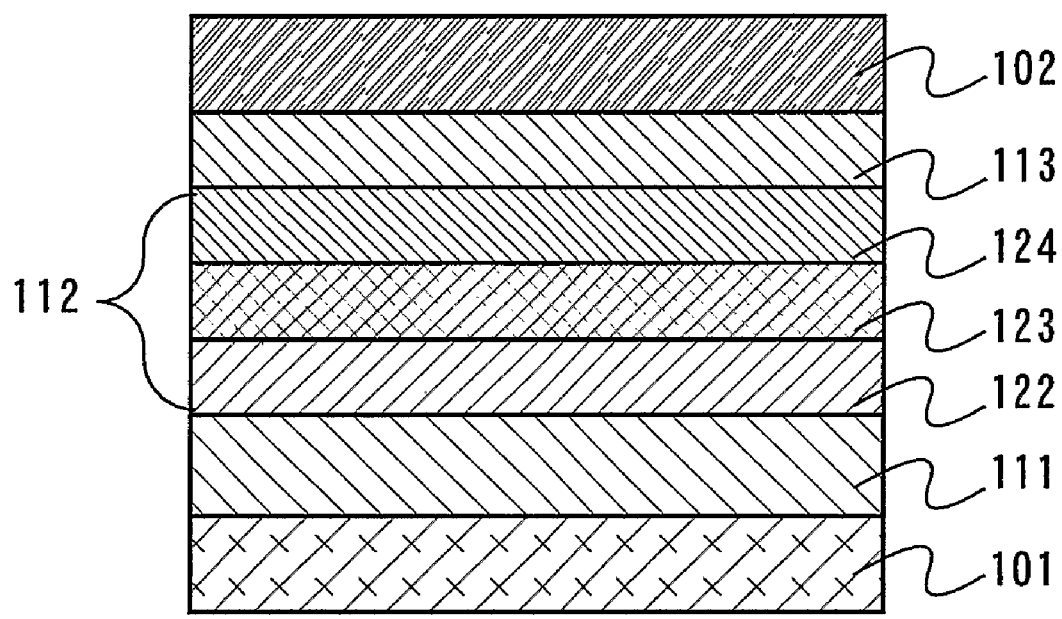
FIG. 18 is a diagram illustrating a light-element according to the present invention.

As shown in FIG. 18, the light-emitting element according to the present invention has a first electrode 101 and a second electrode 102 that are opposed to each other, and has a first layer 111, a second layer 112, and a third layer 113 that are stacked in this order from the first electrode 101 side. When a voltage is applied to this light-emitting element so that the potential of the first electrode 101 is higher than the potential of the second electrode 102, a hole is injected from the first layer 111 into the second layer 112, and an electron is injected from the third layer 113 into the second layer 112. The hole and the electron are recombined to excite a luminescent material. Then, luminescence is produced when the excited luminescent material returns to the ground state.

Next, the first to third layers 111 to 113, the first electrode 101, and the second electrode 102 will be described.

The first layer 111 is a layer that generates holes. This function can be achieved by using, for example, a layer including a hole transporting material and a material that exhibits an electron accepting property to the hole transporting material. In addition, it is preferable that the material that exhibits an electron accepting property to the hole transporting material be included so that the molar ratio of the material to the hole transporting material (=the material that exhibits an electron accepting property to the hole transporting material/the hole transporting material) is 0.5 or more and 2 or less.

The hole transporting material is a material in which electrons are transported more then electrodes, and for example, organic compounds, aromatic amine compounds such as 4,4'-bis[N-(1-naphthyl)-N-phenylamino]biphenyl (abbreviation: α-NPD), 4,4'-bis[N-(3-methylphenyl)-N-phenylamino]biphenyl (abbreviation: TPD), 4,4',4''-tris(N,N-diphenylamino)triphenylamine (abbreviation: TDATA), 4, 4',4''-tris[N-(3-methylphenyl)-N-phenylamino]-triphenylamine (abbreviation: MTDATA), 4,4'-bis[N-{4-(N,N-di-m-tolylamino)phenyl}-N-phenylamino]biphenyl (abbreviation: DNTPD), and phthalocyanine compounds such as phthalocyanine (abbreviation: $H_2Pc$) and copper phthalocyanine (abbreviation: CuPc), can be used as the hole transporting material. It is to be noted that the hole transporting material is not to be considered limited to these.

In addition, an oxide of a transition metal belonging to any one of Group 4 to 12 of the periodic table can be used as the material that exhibits an electron accepting property to the hole transporting material. Among others, an oxide of a transition metal belonging to any one of Groups 4 to 8 of the periodic table often has a higher electron accepting property, and a vanadium oxide, a molybdenum oxide, a niobium oxide, a rhenium oxide, a tungsten oxide, a ruthenium oxide, a titanium oxide, a chromium oxide, a zirconium oxide, a hafnium oxide, and a tantalum oxide are particularly preferable. Besides the oxides, nitrides and oxynitrides of the metals mentioned above may be used. It is to be noted that the material that exhibits am electron accepting property to the hole transporting material is not to be considered limited to these.

When the first layer 111 is formed by using a layer in which the hole transporting material, which is composed of an organic material, and the material that exhibits an electron transporting material to the hole transporting material, which is composed the inorganic material mentioned above, are mixed, the conductivity thereof gets higher. Therefore, it is preferable to form the first layer 111 in this way. When the conductivity is higher, the first layer 111 can be made thicker, and the yield of manufacturing can be thus improved. Further, the first electrode 101 and the second layer 112 can be kept further away from each other by making the first layer 111 thicker. Accordingly, quenching of luminescence due to a metal can be prevented.

Crystallization of the organic compound that is used for the first layer 111 can be suppressed by using this layer in which the organic material and the inorganic material are mixed, and the first layer 111 can be thus formed to be thicker without increase in resistance. Therefore, even when there is irregularity due to dust, contamination, and the like on a substrate, the irregularity has almost no influence since the first layer 111 is made thicker. Accordingly, defects such as a short circuit between the first electrode 101 and the second electrode 102 due to irregularity can be prevented.

As will be described in further detail below in the example, it is determined that the first layer 111 is not likely to be deteriorated with time when a layer in which a benzidine derivative and a molybdenum oxide that is an inorganic compound are mixed is used for the first layer 111. In short, this structure makes it possible to provide a light-emitting element that is excellent in stability.

Further, the first layer 111 may include another organic compound. As the organic compound, rubrene and the like can be cited. The reliability can be improved by the addition of rubrene.

In addition to this, the first layer 111 may be a layer composed of a metal oxide such as a molybdenum oxide, a vanadium oxide, a ruthenium oxide, a cobalt oxide, and a copper oxide.

This first layer 111 can be formed by evaporation. When a layer including a plurality of mixed compounds is used as the first layer 111, co-evaporation can be used. The co-evaporation includes co-evaporation by resistance-heating evaporation, co-evaporation by electron-beam evaporation, and co-evaporation by resistance-heating evaporation and electron-beam evaporation, and in addition, there are methods such as deposition by resistance-heating evaporation and sputtering and deposition by electron-beam evaporation and sputtering. The first layer 111 can be formed by combining the same type of methods or different types of methods. In addition, the example described above shows a layer including two kinds of materials. However, when three or more kinds of materials are included, the first layer 111 can be formed also in the same way by combining the same type of methods or different types of methods as described above.

Next, the second layer 112 that is a layer including a light-emitting layer will be described. The layer including the light-emitting layer may be a single layer composed of only the light-emitting layer or a multilayer. To cite a case, a specific multilayer includes a light-emitting layer and additionally a plurality of layers selected from electron transporting layers and hole transporting layers. In FIG. 1, a multilayer case in which the second layer 112 includes a light-emitting layer 123, an electron transporting layer 124, and a hole transporting layer 124 is shown.

A benzidine derivative according to the present invention, which is represented by a general formula (1) or any one of structure formulas (2) to (4), can be used for the hole transporting layer 112.

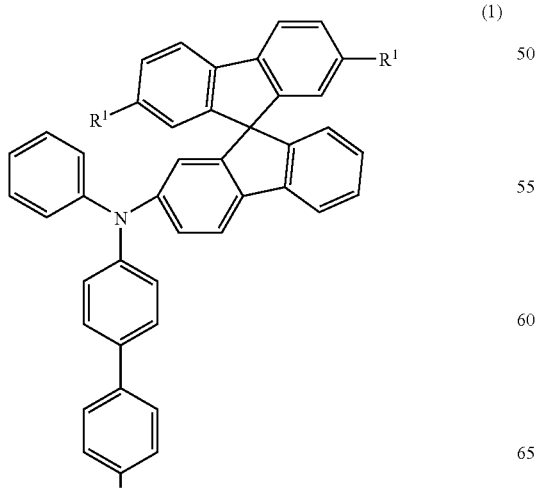

(1)

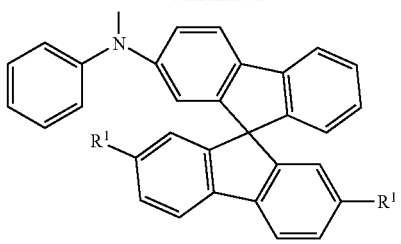

(2)

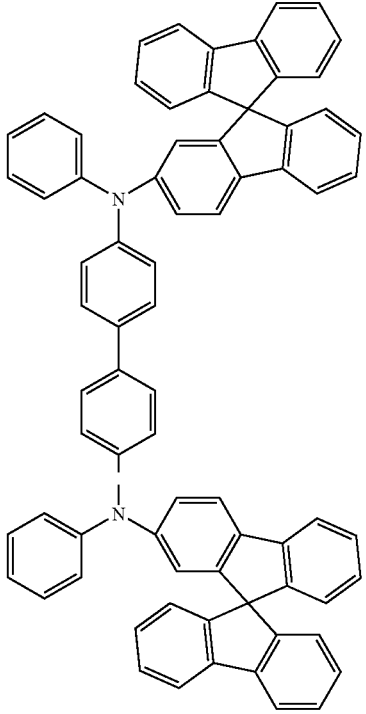

(3)

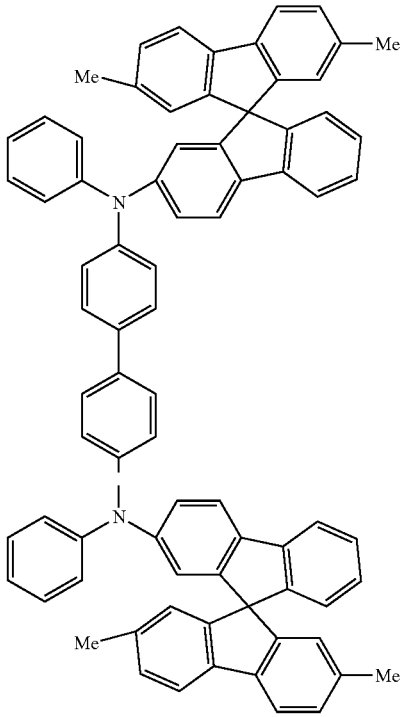

-continued

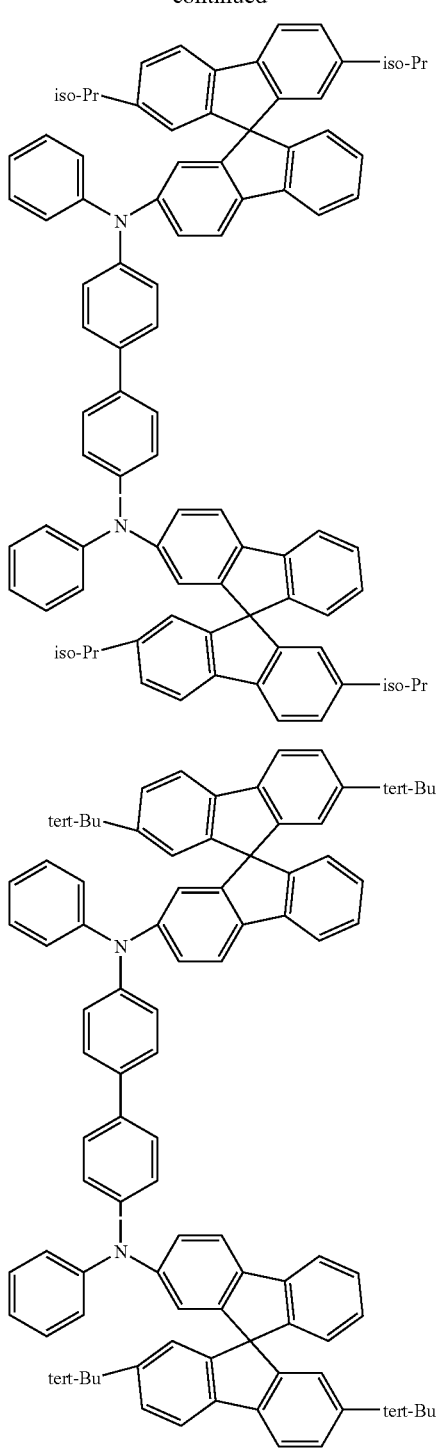

(4)

(5)

Since the benzidine derivative according to the present invention has high heat resistance, the hole transporting layer 122 that is less likely to change in characteristics due to heat can be formed by using the benzidine derivative according to the present invention as a hole transporting material. Further, since the benzidine derivative according to the present invention is not likely to be crystallized, the hole transporting layer 122 that is not likely to be crystallized can be formed by using the benzidine derivative according to the present invention as a hole transporting material.

It is to be noted that the hole transporting layer 112 may be a multilayer formed by combining two or more layers each including the benzidine derivative according to the present invention, which is represented by the general formula (1) or any one of the structure formulas (2) to (4).

Further, it is preferable that a layer in which the benzidine derivative according to the present invention and an inorganic compound are mixed be used for the hole transporting layer 122. Crystallization of the benzidine derivative can be further suppressed by mixing the inorganic compound, and the layer can be thus formed to be thicker without increase in resistance. Therefore, even when there is irregularity due to dust, contamination and the like, on a substrate, the irregularity has almost no influence since the hole transporting layer 122 is made thicker. Accordingly, defects such as a short circuit between the first electrode 101 and the second electrode 102 due to irregularity can be prevented.

Metal oxides, metal nitrides, and metal oxynitrides can be used for this inorganic compound. For example, an oxide of a transition metal belonging to any one of Group 4 to 12 of the periodic table can be used as a metal oxide. Among others, an oxide of a transition metal belonging to any one of Groups 4 to 8 of the periodic table often has a higher electron accepting property, and a vanadium oxide, a molybdenum oxide, a niobium oxide, a rhenium oxide, a tungsten oxide, a ruthenium oxide, a titanium oxide, a chromium oxide, a zirconium oxide, a hafnium oxide, and a tantalum oxide are particularly preferable.

Next, the light-emitting layer 123 will be described. It is preferable that the light-emitting layer 123 be a layer including a luminescent material dispersed in a material that has a larger energy gap than the luminescent material. However, the light-emitting layer 123 is not to be considered limited to this. It is to be noted that the energy gap indicates the energy gap between the LUMO level and the HOMO level. In addition, a material that provides a favorable luminous efficiency and is capable of producing luminescence of a desired emission wavelength may be used for the luminescent material.

In addition, for the material that is used for dispersing the luminescent material, for example, anthracene derivatives such as anthracene derivatives such as 9,10-di(2-naphthyl)-2-tert-butylanthracene (abbreviation: t-BuDNA), carbazole derivatives such as 4,4'-bis(N-carbazolyl)-biphenyl (abbreviation: CBP), and metal complexes such as bis[2-(2-hydroxyphenyl)-pyridinato]zinc (abbreviation: $Znpp_2$) and bis[2-(2-hydroxyphenyl)-benzoxazolato]zinc (abbreviation: ZnBOX) can be used. However, the material that is used for dispersing the luminescent material is not limited to these materials. When the luminescent material is dispersed as described above, concentration quenching of luminescence from the luminescent material can be prevented.

In order to produce white or whitish light emission from this light-emitting layer 123, for example, a structure of TPD (aromatic diamine), 3-(4-tert-butylphenyl)-4-phenyl-5-(4-biphenylyl)-1,2,4-triazole (abbreviation: TAZ), tris(8-quinolinolato) aluminum (abbreviation: $Alq_3$), $Alq_3$ doped with NileRed that is a red luminescent dye, and $Alq_3$ that are laminated by evaporation or the like in this order from the first electrode 101 side can be used.

In addition, a structure of NPB, NPB doped with perylene, bis(2-methyl-8-quinolinolato)-4-phenylphenolato-aluminum (abbreviation: BAlq) doped with DCM1, BAlq, and $Alq_3$ that are laminated by evaporation or the like in this order from the first electrode 101 side can be used.

In addition, white or whitish light emission can be obtained by dispersing 30 wt % 2-(4-biphenylyl)-5-(4-tert-butylphenyl)-1,3,4-oxadiazole (abbreviation: PBD) as an electron transporting agent in poly(N-vinylcarbasole) (abbreviation: PVK) and dispersing appropriate amounts of four kinds of dyes (TPB, coumarin 6, DCM 1, and NileRed).

Moreover, white or whitish light emission can be also obtained by forming the light-emitting layer 123 using a laminated structure with the use of materials that produce luminescence in relation of complementary colors to each other, for example, a first and second layers using luminescent materials for red and blue-green, respectively.

In the case of emitting white or whitish light as described above, full-color display can be performed with the use of a color filter or a color conversion layer. It is to be noted that mono-color display can be performed in the case of using a monochromatic color filter or a monochromatic color conversion layer.

Further, materials for the light-emitting layer 123 can be appropriately selected besides the light-emitting elements described above, which provide white or whitish light emission. For example, the light-emitting layer 123 may be formed by using respective luminescent materials for red (R), green (G), and blue (B).

For example, when red or reddish luminescence is desired to be obtained, 4-dicyanomethylene-2-isopropyl-6-[2-(1,1,7,7-tetramethyljulolidine-9-yl)ethenyl]-4H-pyran (abbreviation: DCJTI), 4-dicyanomethylene-2-methyl-6-[2-(1,1,7,7-tetramethyljulolidine-9-yl)ethenyl]-4H-pyran (abbreviation: DCJT), 4-dicyanomethylene-2-tert-butyl-6-[2-(1,1,7,7-tetramethyljulolidine-9-yl)ethenyl]-4H-pyran (abbreviation: DCJTB), periflanthene, and 2,5-dicyano-1,4-bis-[2-(10-methoxy-1,1,7,7-tetramethyljulolidine-9-yl)ethenyl]-benzene, bis[2,3-bis(4-fluorophenyl)quinoxalinato]iridium (acetylacetonato) (abbreviation: Ir(Fdpq)$_2$(acac)), and the like can be used for the light-emitting layer 123. However, the material for obtaining red or reddish luminescence is not limited to these materials, and a material that produces luminescence with an emission spectrum peak from 600 nm to 700 nm can be used.

When green or greenish luminescence is desired to be obtained, N,N'-dimethylquinacridone (abbreviation: DMQd), coumarin 6, coumarin 545T, tris(8-quinolinolato) aluminum (abbreviation: Alq$_3$), and the like can be used for the light-emitting layer 123. However, the material for obtaining green or greenish luminescence is not limited to these materials, and a material that produces luminescence with an emission spectrum peak from 500 nm to 600 nm can be used.

In addition, when blue or bluish luminescence is desired to be obtained, 9,10-bis(2-naphthyl)-tert-butylanthracene (abbreviation: t-BuDNA), 9,9'-bianthryl, 9,10-diphenylanthracene (abbreviation: DPA), 9,10-bis(2-naphthyl)anthracene (abbreviation: DNA), bis(2-methyl-8-quinolinolato)-4-phenylphenolato-gallium (abbreviation: BGaq), bis(2-methyl-8-quinolinolato)-4-phenylphenolato-aluminum (abbreviation: BAlq), and the like can be used for the light-emitting layer 123. However, the material for obtaining blue or bluish luminescence is not limited to these materials, and a material that produces luminescence with an emission spectrum peak from 400 nm to 500 nm can be used.

Also, when the light-emitting layer 123 is formed to include respective luminescent materials for red (R), green (G), and blue (B), the peak of each emission spectra and the like may be adjusted by providing a color filter or a color conversion layer. A color filter or a color conversion layer may be formed on the side from which light emission is extracted outside, or can be provided on any of the substrate side where a thin film transistor is formed and the opposed substrate side.

Next, the electron transporting layer 124 will be described. The electron transporting layer 124 is a layer that has a function of transporting electrons injected from the second electrode 102 to the light-emitting layer 123. By providing the electron transporting layer 124 in this way to keep the second electrode 102 and the light-emitting layer 123 further away from each other, quenching of luminescence due to a metal can be prevented.

It is to be noted that the electron transporting layer 124 is not particularly limited, and can be formed by using a metal complex having a quinoxaline skeleton or a benzoquinoline skeleton, such as tris(8-quinolinolato) aluminum (abbreviation: Alq$_3$), tris(4-methyl-8-quinolinolato) aluminum (abbreviation: Almq$_3$), bis(10-hydroxybenzo[h]-quinolinato) beryllium (abbreviation: BeBq$_2$), and bis(2-methyl-8-quinolinolato)-4-phenylphenolato-aluminum (abbreviation: BAlq). In addition, the electron transporting layer 124 may be formed by using a metal complex having an oxazole-based or thiazole-based ligand, such as bis[2-(2-hydroxyphenyl)-benzoxazolato]zinc (abbreviation: Zn(BOX)$_2$) and bis[2-(2-hydroxyphenyl)-benzothiazolato]zinc (abbreviation: Zn(BTZ)$_2$). Moreover, the electron transporting layer 124 may be formed by using 2-(4-biphenylyl)-5-(4-tert-butylphenyl)-1,3, 4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or the like.

It is preferable that the electron transporting layer 124 be formed with the use of a material in which the hole mobility is higher than the electron mobility. Further, it is more preferable that the electron transporting layer 124 be formed with the use of a material that has an electron mobility of $10^{-6}$ cm$^2$/Vs or more. In addition, the electron transporting layer 124 may have a laminated structure formed by combining two or more layers each including the material described above.

Further, it is preferable that a layer in which the organic compound described above and an inorganic compound are mixed is used for the electron transporting layer 124. Crystallization of the organic compound can be further suppressed by mixing the inorganic compound, and the layer can be thus formed to be thicker without increase in resistance. Therefore, even when there is irregularity due to dust, contamination, and the like on a substrate, the irregularity has almost no influence by to the electron transporting layer 124 is made thicker. Accordingly, defects such as a short circuit between the first electrode 101 and the second electrode 102 due to irregularity can be prevented.

Metal oxides, metal nitrides, and metal oxynitrides can be used for this inorganic compound. For example, the metal oxides include a lithium oxide (Li$_2$O), a calcium oxide (CaO), a sodium oxide (Na$_2$O), a potassium oxide (K$_2$O), a magnesium oxide (MgO), and further include a lithium fluoride (LiF), a cesium fluoride (CsF), and calcium fluoride (CaF$_2$).

This second layer 112 can be manufactured by evaporation. When a mixed layer is formed for the second layer 112, co-evaporation can be used. The co-evaporation includes co-evaporation by resistance-heating evaporation, co-evaporation by electron-beam evaporation, and co-evaporation by resistance-heating evaporation and electron-beam evaporation, and in addition, there are methods such as deposition by resistance-heating evaporation and sputtering and deposition by electron-beam evaporation and sputtering. The first layer 111 can be formed by combining the same type of methods or different types of methods. In addition, the example described above shows a layer including two kinds of materials. However, when three or more kinds of materials are included, the first layer 111 can be formed also in the same way by combining the same type of methods or different types of methods as described above.

Next, the third layer 113 that is layer that generates electrons will be described. As this third layer 113, for example, a layer including an electron transporting material and a material that exhibits an electron donating property to the electron transporting material can be cited.

It is to be noted that the electron transporting material is a material in which more electrons are transported than holes, and for example, metal complexes such as tris (8-quinolinolato) aluminum (abbreviation: $Alq_3$), tris(4-methyl-8-quinolinolato) aluminum (abbreviation: $Almq_3$), bis(10-hydroxybenzo[h]-quinolinato)beryllium (abbreviation: $BeBq_2$), bis (2-methyl-8-quinolinolato)-4-phenylphenolato-aluminum (abbreviation: BAlq), bis[2-(2-hydroxyphenyl)-benzoxazolato]zinc (abbreviation: $Zn(BOX)_2$), and bis[2-(2-hydroxyphenyl)-benzothiazolato]zinc (abbreviation: $Zn(BTZ)_2$), and further, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), and 4,4-bis(5-methylbenzoxazol-2-yl)stilbene (abbreviation: BzOs) can be used for the electron transporting material. In addition, the third layer 113 can be formed with the use of an n-type semiconductor. However, the electron transporting material is not limited to these.

In addition, for the material that exhibits an electron donating property to the electron transporting material, a substance selected from alkali metals and alkali-earth metals, specifically such as lithium (Li), calcium (Ca), sodium (Na), potassium (K), and magnesium (Mg), can be used. Further, specific materials include oxides of the alkali metals, oxides of the alkali-earth metals, nitrides of the alkali metals, and nitrides of the alkali-earth metals, specifically, a lithium oxide ($Li_2O$), a calcium oxide (CaO), a sodium oxide ($Na_2O$), a potassium oxide ($K_2O$), and a magnesium oxide (MgO), and further include lithium fluoride (LiF), cesium fluoride (CsF), and calcium fluoride ($CaF_2$). However, the material that exhibits an electron donating property to the electron transporting material is not limited to these. It is to be noted that it is preferable that the material that exhibits an electron donating property to the electron transporting material be included so that the molar ratio of material that exhibits an electron donating property to the electron transporting material to the electron transporting material is 0.5 or more and 2 or less (=the material that exhibits an electron donating property to the electron transporting material/the electron transporting material).

Alternatively, the third-layer 113 may be a layer composed of a material such as zinc oxide, zinc sulfide, zinc selenide, tin oxide, or titanium oxide.

The third layer 113 is preferably formed by using a layer in which the above-mentioned organic compound and an inorganic compound are mixed. Accordingly, the conductivity of the third layer 113 can be made higher. When the conductivity is higher, the third layer 113 can be made thicker, and the yield of manufacturing can be thus improved. Further, the light-emitting layer 123 and the second electrode 102 can be kept further away from each other by making the third layer 113 thicker, and quenching of luminescence can be thus prevented.

Further, crystallization of the organic compound that is used for the third layer 113 can be suppressed by using the layer in which the organic material and the inorganic material are mixed, and the third layer 113 can be thus formed to be thicker without increase in resistance. Therefore, even when there is irregularity due to dust, contamination, and the like on a substrate, the irregularity has almost no influence since the third layer 113 is made thicker. Accordingly, defects such as a short circuit between the first electrode 101 and the second electrode 102 due to irregularity can be prevented.

This third layer 113 can be manufactured by evaporation. When a mixed layer is formed for the third layer 113, co-evaporation can be used. The co-evaporation includes co-evaporation by resistance-heating evaporation, co-evaporation by electron-beam evaporation, and co-evaporation by resistance-heating evaporation and electron-beam evaporation, and in addition, there are methods such as deposition by resistance-heating evaporation and sputtering and deposition by electron-beam evaporation and sputtering. The first layer 111 can be formed by combining the same type of methods or different types of methods. In addition, the example described above shows a layer including two kinds of materials. However, when three or more kinds of materials are included, the first layer 111 can be formed also in the same way by combining the same type of methods or different types of methods as described above.

In the light-emitting element described above, the difference between the electron affinity of the electron transporting material included in the third layer 113 and the electron affinity of the material included in the layer in contact with the third layer 113 among the layers included in the second layer 112 is preferably 2 eV or less, more preferably 1.5 eV or less. Alternatively, when the third layer 113 is composed of an n-type semiconductor, the difference between the work function of the n-type semiconductor and the electron affinity of the material included in the layer in contact with the third layer 113 among the layers included in the second layer 112 is preferably 2 eV or less, more preferably 1.5 eV or less. By joining the second layer 112 and the third layer 113 as described above, electrons can be injected more easily from the third layer 113 to the second layer 112.

It is to be noted that the present invention has a feature of a light-emitting element including an organic compound as typified by a benzidine derivative and an inorganic compound between a pair of electrodes, and is not to be considered limited to the structure of the light-emitting element shown in FIG. 18. For example, there may be a case where the electron transporting layer 124 is not provided although the structure provided with the electron transporting layer 124 formed in contact with the third layer 113 is shown. Accordingly, the light-emitting layer 123 in contact with the third layer 113 is provided. In this case, a material for dispersing a luminescent material is preferably used for the light-emitting layer 123. Also, it may well be that the electron transporting layer 124 is not provided.

In addition, a material that is capable of producing luminescence without being dispersed, such as $Alq_3$, can be used for the light-emitting layer 123. Since the material such as $Alq_3$ is a luminescent material that has a favorable carrier transporting property, a layer composed of only $Alq_3$ can function as a light-emitting layer without dispersing $Alq_3$. In this case, the light-emitting layer 123 corresponds to a luminescent material itself.

These first to third layers 111 to 113 can be formed by the same method, and can be therefore formed continuously without being exposed to the air. Impurity mixing into an interface and the like can be reduced by forming the first to third layers 111 to 113 continuously without being exposed to the air in this way.

Next, the electrodes will be described. Each of the first electrode 101 and the second electrode 102 are formed by using a conductive material. Further, the electrode provided on the side from which light from the light-emitting layer is extracted outside needs to have a light-transmitting property in addition to conductivity. The light-transmitting property can be obtained also by forming a quite thin film composed of a material that has no light-transmitting property.

As a material for the first electrode 101, light-transmitting materials such as indium tin oxide (ITO), indium tin oxide containing silicon oxide (ITSO), and indium oxide containing zinc oxide, and in addition, metal materials such as gold (Au), platinum (Pt), nickel (Ni), tungsten (W), chromium (Cr), molybdenum (Mo), iron (Fe), cobalt (Co), copper (Cu), and palladium (Pd) can be used in addition to aluminum (Al). Further, the first electrode 101 can be formed, for example, by sputtering or evaporation. However, the material for the first electrode 101 is not limited to these.

When the above-mentioned material that has no light-transmitting property is used and the first electrode 101 needs to have a light-transmitting property, a thin film composed of the material may be formed.

In addition, a single layer of the metal material mentioned above or a lamination layer can be used for the first electrode 101. Therefore, when a lamination layer is used for the first electrode 101, it is also possible to use a structure of forming a thin film of the material mentioned above and laminating a light-transmitting material thereon. Of course, the first electrode 101 may be formed with the use of the thin material as a single layer. In order to prevent the resistance from increasing by forming the first electrode 101 to be thin, an auxiliary wiring can also be provided. Further, the use of a lamination layer can prevent the resistance from increasing.

Further, as a material for the second electrode 102, light-transmitting materials such as indium tin oxide (ITO), indium tin oxide containing silicon oxide (hereinafter, also referred to as ITSO), and indium oxide containing zinc oxide, and metal materials such as gold (Au), platinum (Pt), nickel (Ni), tungsten (W), chromium (Cr), molybdenum (Mo), iron (Fe), cobalt (Co), copper (Cu), and palladium (Pd) can be used. However, the material for the first electrode 101 is not limited to these.

When the above-mentioned material that has no light-transmitting property is used and the second electrode 102 needs to have a light-transmitting property, a thin film composed of the material may be formed.

In addition, a single layer of the metal material mentioned above or a lamination layer can be used for the second electrode 102. Therefore, when a lamination layer is used for the second electrode 102, it is also possible to use a structure of forming a thin film of the material mentioned above and laminating a light-transmitting material thereon. Of course, the second electrode 102 may be formed with the use of the thin material as a single layer. In order to prevent the resistance from increasing by forming the second electrode 102 to be thin, an auxiliary wiring can also be provided. Further, the use of a lamination layer can prevent the resistance from increasing.

It is to be noted that the first electrode 101 or the second electrode 103 can be an anode or a cathode depending on a voltage that is applied to the light-emitting element. In the case of an anode, a material that has a larger work function (a work function of 4.0 eV or more) is used. Alternatively, in the case of a cathode, a material that has a smaller work function (a work function of 3.8 eV or less) is used.

The first electrode 101 or the second electrode 102 can be formed by sputtering, evaporation, or the like. In the case of using evaporation, the first electrode 101, the first to third layers 111 to 113, and the second electrode 102 can be formed continuously without being exposed to the air. Impurity mixing into an interface and the like can be reduced by forming the light-emitting element continuously without being exposed to the air in this way.

As described above, according to the present invention, a light-emitting element that is less likely to change in characteristics by change in characteristics of a hole transporting layer due to heat can be obtained by forming a layer that generates holes with the use of a layer including an organic compound as typified by a benzidine derivative and an inorganic compound. Further, by forming a layer that generates holes with the use of a layer including an organic compound as typified by a benzidine derivative and an inorganic compound, a light-emitting element that is less likely to be deteriorate by crystallization of the layer can be obtained.

Accordingly, a light-emitting element achieving a lower driving voltage can be obtained. Further, even when the light-emitting element according to the present invention is made thicker, the driving voltage is not increased. Accordingly, the light-emitting element can be formed to be thicker, and can be thus produced at a favorable yield. Further, a light-emitting layer can be kept further away from a first electrode or a second electrode by making a layer thicker, and quenching of luminescence can be thus prevented.

Embodiment 3

In the present embodiment, the structure of a light-emitting element that is different from the embodiments-described above will be described.

Figure 2:
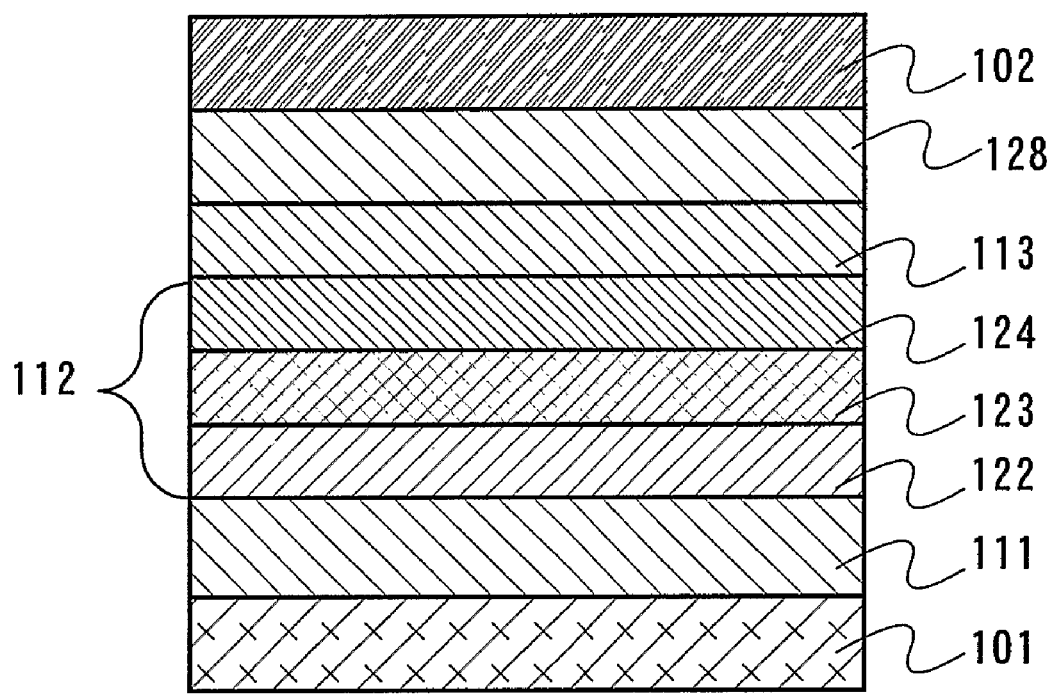
FIG. 2 is a diagram illustrating a light-emitting element according to the present invention.

As shown in FIG. 2, the light-emitting element shown in the present embodiment has a first electrode 101 and a second electrode 102 that are opposed to each other, and has a first layer 111, a second layer 112, a third layer 113, and a fourth layer 128 that are stacked in this order from the first electrode 101 side, where it is a feature that the fourth layer 128 is provided. The fourth layer 128 can be formed by using the same material as the first layer 111, and the other structure is the same as the embodiment described above. Therefore, description of the structure other than the fourth layer 128 is omitted.

When the fourth layer 128 is provided in this way, damage during forming the second electrode 102 can be further reduced.

Further, a layer in which an organic compound and an inorganic compound are mixed is preferably used for the fourth layer 128. Metal oxides, metal nitrides, and metal oxynitrides can be used for this inorganic compound. For example, an oxide of a transition metal belonging to any one of Group 4 to 12 of the periodic table can be used as a metal oxide. Among others, an oxide of a transition metal belonging to any one of Groups 4 to 8 of the periodic table often has a higher electron accepting property, and a vanadium oxide, a molybdenum oxide, a niobium oxide, a rhenium oxide, a tungsten oxide, a ruthenium oxide, a titanium oxide, a chromium oxide, a zirconium oxide, a hafnium oxide, and a tantalum oxide are particularly preferable.

When the organic compound and the inorganic compound are mixed in this way, the driving voltage can be kept lower even when the fourth layer 128 is made thicker.

Embodiment 4

In the present embodiment, a benzidine derivative that is an organic compound that has a glass-transition temperature of 150° C. or more, preferably 160° C. or more and 300° C. or less, and has a spiro ring and a triphenylamine skeleton will be described with reference to a general formula.

An aspect of the present invention is a benzidine derivative represented by a general formula (1).

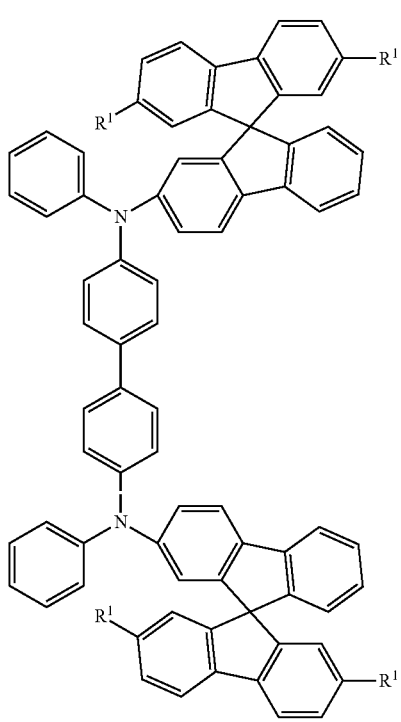

(1)

In the general formula (1), R¹ is hydrogen or an alkyl group having 1 to 4 carbon atoms.

A benzidine derivative according to the present invention is a compound that is obtained by a coupling reaction of N,N'-diphenylbenzidine with 2-bromo-spiro-9,9'-bifluorene or 2-bromo-2',7'-dialkyl-spiro-9,9'-bifluorene.

A light-emitting element according to the present invention is a light-emitting element that has a layer including an organic compound that is a compound that is obtained by a coupling reaction of N,N'-diphenylbenzidine with 2-bromo-spiro-9,9'-bifluorene.

The benzidine derivative according to the present invention has a feature that the glass-transition temperature meets 150° C. or more, preferably 160° C. or more and 300° C. or less, and a feature that the melting point meets 180° C. or more and 400° C. or less.

Since the benzidine derivative according to the present invention has excellent heat resistance, a light-emitting element that is less likely to change in characteristics due to heat can be obtained by using the benzidine derivative according to the present invention. Further, since the benzidine derivative according to the present invention can be easily kept amorphous, a light-emitting element that is less likely to be deteriorated due to crystallization can be obtained by using the benzidine derivative according to the present invention.

Embodiment 5

In the present embodiment, an organic compound as typified by a benzidine derivative that has a glass-transition temperature of 150° C. or more, preferably 160° C. or more and 300° C. or less, and has a spiro ring and a triphenylamine skeleton will be described with reference to structure formulas (2) to (5).

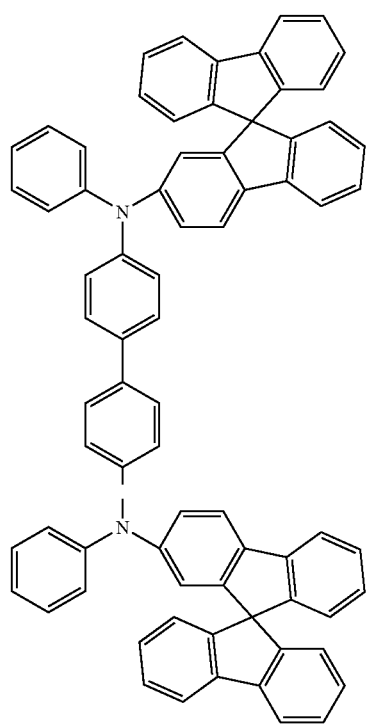

(2)

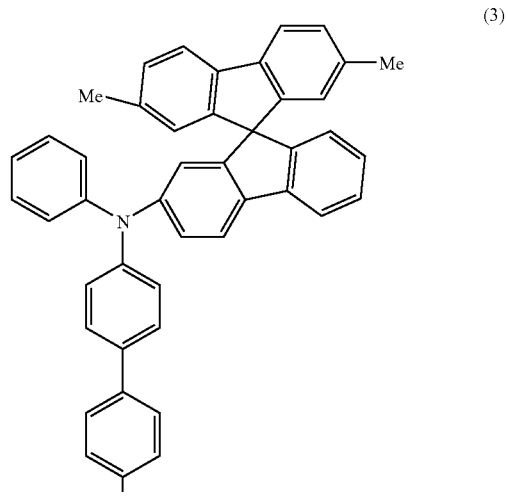

(3)

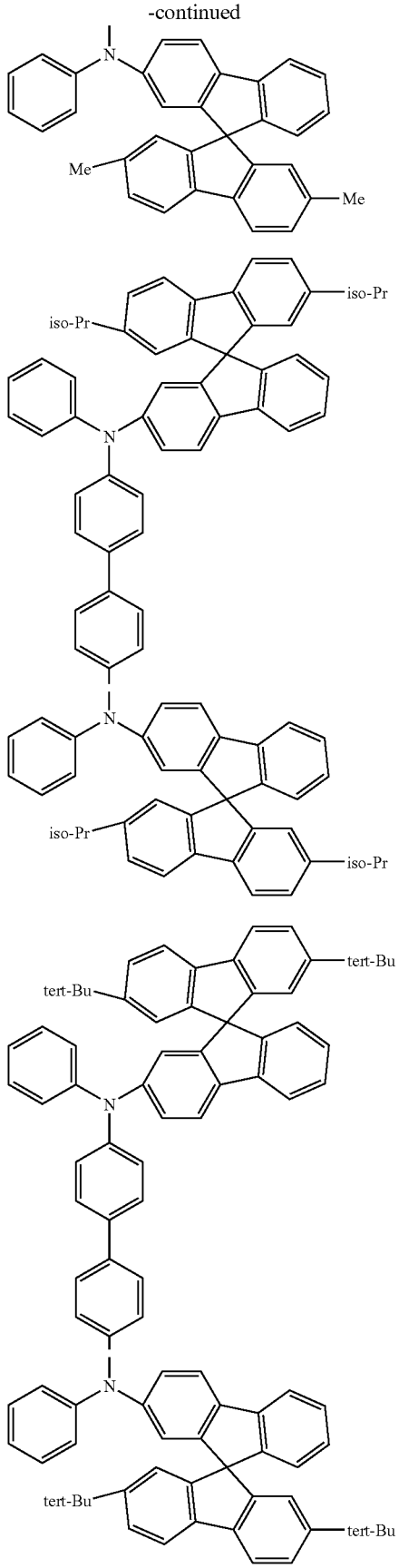

(4)

(5)

The benzidine derivatives represented by structural formulas (2) to (5) have high glass-transition temperatures of 150° C. or more, preferably 160° C. or more and 300° C. or less and have excellent heat resistance. Further, the benzidine derivatives represented by structural formulas (2) to (5) are not likely to be crystallized. Moreover, the benzidine derivatives represented by structural formulae (2) to (5) have high melting temperature of 180° C. or more and 400° C. or less.

Although the synthesis method of the benzidine derivative according to the present invention is not particularly limited, the benzidine derivative can be synthesized by a coupling reaction of N,N'-diphenylbenzidine with 2-bromo-spiro-9,9'-bifluorene or 2-bromo-2',7'-dialkyl-spiro-9,9'-bifluorene as represented by a synthesis scheme (a-1).

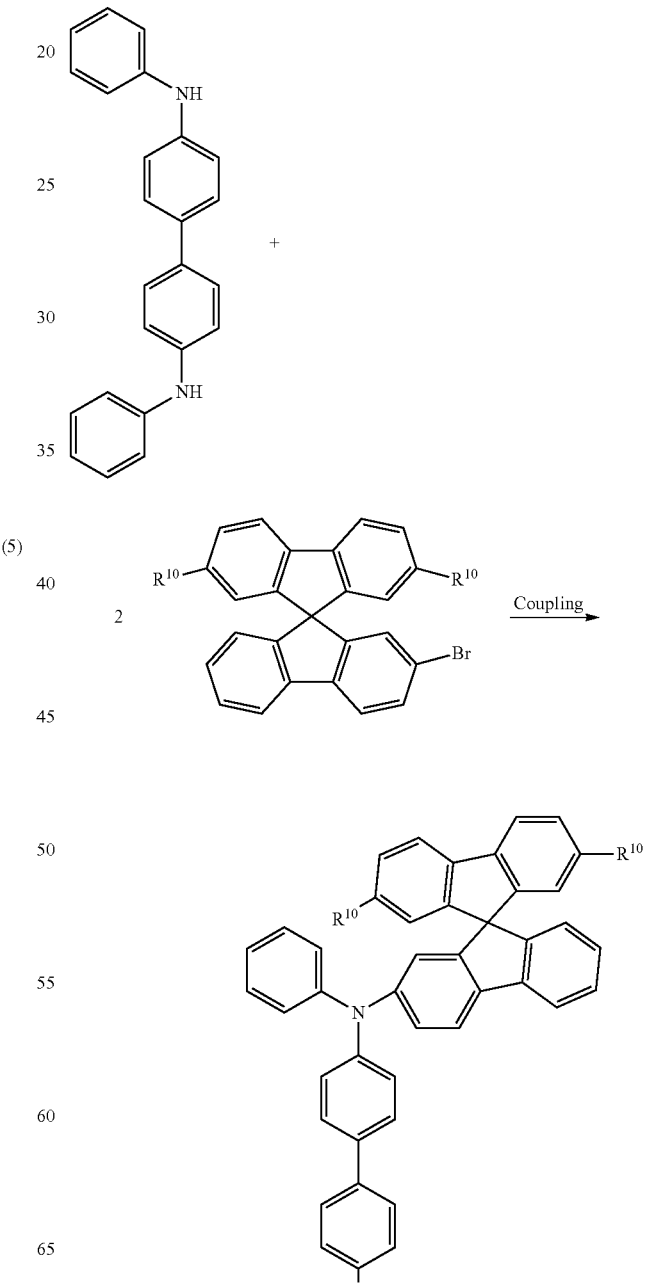

-continued

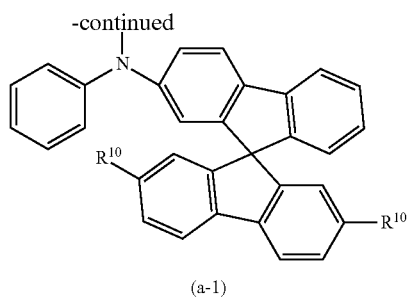

(a-1)

In the synthesis scheme (a-1), $R^{10}$ is hydrogen or an alkyl group having 1 to 4 carbon atoms. It is preferable here that an alkyl group having 3 or 4 carbon atoms be preferably in a state of branching.

The thus described benzidine derivative according to the present invention can be used as a material for forming a hole transporting layer, that is, a hole transporting material.

The benzidine derivative according to the present invention has a feature that the glass-transition temperature meets 150° C. or more, preferably 160° C. or more and 300° C. or less, and a feature that the melting point meets 180° C. or more and 400° C. or less.

Since the benzidine derivative according to the present invention has excellent heat resistance, a light-emitting element that is less likely to change in characteristics due to heat can be obtained by using the benzidine derivative according to the present invention. Further, since the benzidine derivative according to the present invention can be easily kept amorphous, a light-emitting element that is less likely to be deteriorated due to crystallization can be obtained by using the benzidine derivative according to the present invention.

Embodiment 6

A light-emitting element according to the present invention can be applied to a pixel portion of a light-emitting device that has a display function and a lighting portion of a light-emitting device that has a lighting function. Further, since the light-emitting element according to the present invention is less likely to change in characteristics due to heat and less likely to be deteriorated due to crystallization, a light-emitting device that has fewer image defects or fewer defects of irradiated light due to deterioration of the light-emitting element can be obtained by using the light-emitting element according to the present invention. Now, in the present embodiment, the cross-sectional structure of a pixel portion including the light-emitting element will be described.

Figure 3A:
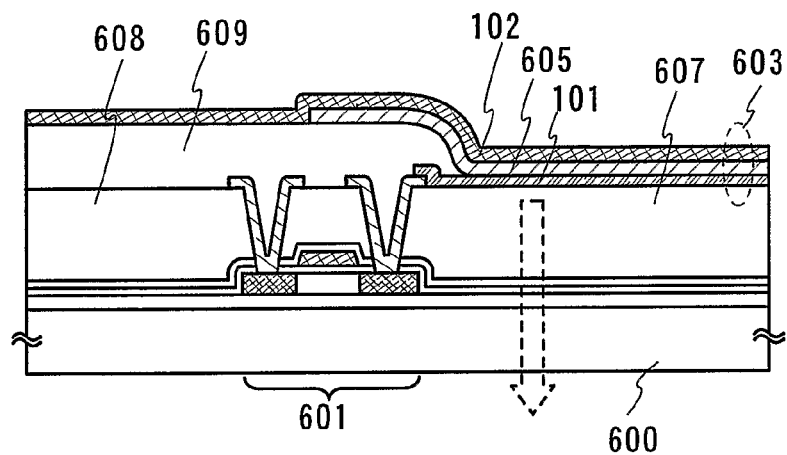
FIGS. 3A to 3C are cross-sectional views illustrating light-emitting elements according to the present invention.
Figure 3B:
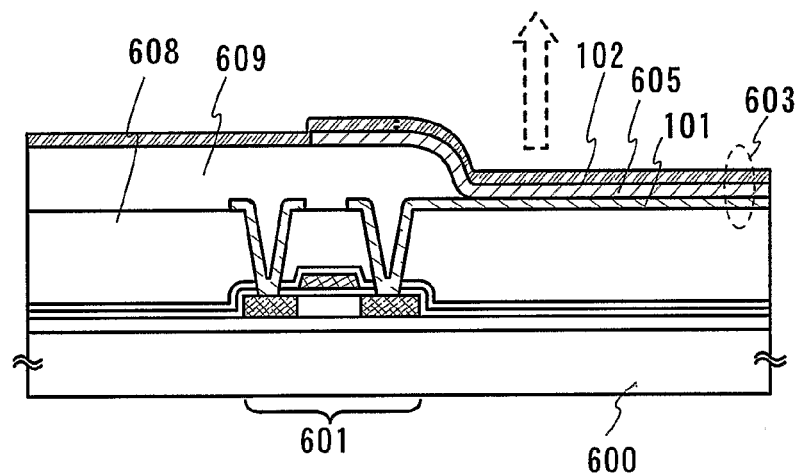
Figure 3C:
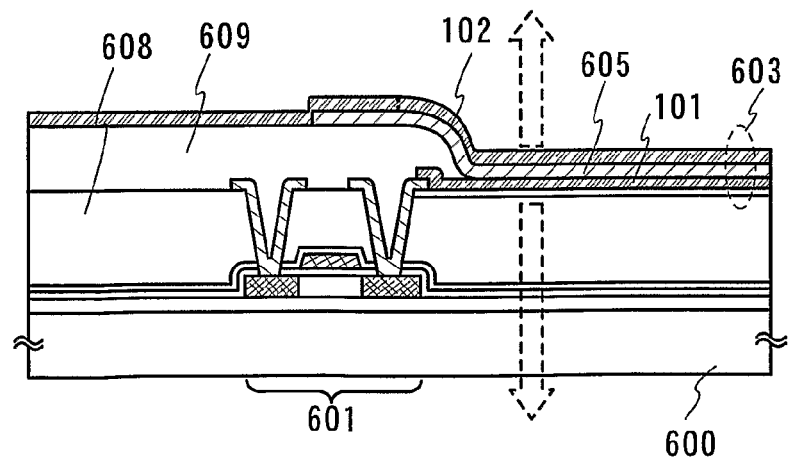

FIGS. 3A to 3C show cross-sectional views in which a p-channel thin film transistor (TFT) is used as a semiconductor element that controls supply of current to a light-emitting element, and a case in which a first electrode of the light-emitting element functions as an anode and a second electrode thereof functions as a cathode will be exemplified.

FIG. 3A shows a cross-sectional view of a pixel where a TFT 601 is a p-channel transistor and light emitted from a light-emitting element 603 is extracted from a first electrode 101 side (in the direction of a dashed arrow). In FIG. 3A, the TFT 601 provided over a substrate 600 has a semiconductor film, a gate electrode that is provided over the semiconductor film with an insulating film interposed therebetween, and a wiring connected to an impurity region formed in the semiconductor film. Further, a wiring of the TFT 601 is electrically connected to the first electrode 101 in the light-emitting element 603.

The TFT 601 is covered with an interlayer insulating film 608, and a partition 609 with an opening is formed on the interlayer insulating film 608. In the opening of the partition 609, the first electrode 101 is partly exposed. The first electrode 101, an electroluminescent layer 605, and a second electrode 102 are stacked in this order in the opening. It is to be noted that the electroluminescent layer 605 in the present embodiment indicates the first layer 111 to the third layer 113, and additionally the fourth layer 128 of in the embodiment described above; namely, the electroluminescent layer 605 indicates the layers between the first electrode 101 and the second electrode 102.

The interlayer insulating film 608 can be formed by using an organic resin film, an inorganic insulating film, or an insulating film including a Si—O—Si bond formed by a siloxane material as a starting material (hereinafter, referred to as a "siloxane insulating film"). It is to be noted that siloxane has a framework structure formed by a bond of silicon (Si) and oxygen (O), in which an organic group containing at least hydrogen (such as an alkyl group or aromatic hydrocarbon) is used as a substituent. Alternatively, a fluoro group may be used as the substituent. Further, an organic group containing at least hydrogen and a fluoro group may also be used as substituents. For the interlayer insulating film 608, a so-called low dielectric constant material (low-k material) may also be used. The interlayer insulating film 608 may be either a single layer or a lamination layer.

The partition 609 can be formed by using an organic resin film, an inorganic insulating film, or a siloxane insulating film. For example, organic resin films such as acrylic, polyimide, and polyamide, and inorganic insulating films such as silicon oxide, silicon nitride oxide, and the like can be used. When a photosensitive organic resin film is used for the partition 609, the opening formed in the organic resin film can be formed so that a side wall of the opening has a slope with a continuous curvature, with the result that the first electrode 101, the electroluminescent layer 605, and the second electrode 102 can be prevented from being disconnected to each other. In addition, the partition 609 may be either a single layer or a lamination layer. Further, since the electroluminescent layer 605 can be made thicker when the light-emitting element according to the present invention is used, a short circuit between the first electrode 101 and a second electrode 102 can be prevented.

In FIG. 3A, in order to extract light emission to the first electrode 101 side (in the direction of the dashed arrow), the first electrode 101 is formed by using a light-transmitting material or formed to have a film thickness through which light is transmitted. In addition to the light-transmitting material mentioned above, for example, a single-layer film including one or more of TiN, ZrN, Ti, W, Ni, Pt, Cr, Ag, Al and the like, a lamination layer of a titanium nitride film and a film including aluminum as its main component, and a three-layer structure of a titanium nitride film, a film including aluminum as its main component, and a titanium nitride film can be used for the first electrode 101. However, when a material other than the light-transmitting material is used, the first electrode 101 is formed to have a film thickness (preferably, approximately 5 to 30 nm) through which light is transmitted. Further, since the TFT 601 is a p-channel transistor, the first electrode 101 is formed by using a material that is suitable for being used as an anode.

The second electrode 102 is formed by using a material that reflects or blocks light or formed to have a film thickness that blocks light. Further, the second electrode 102 is formed by using a material that is suitable for being used as a cathode; namely, can be formed by using a metal, alloy, or electrically conductive compound that has a smaller work function, or a mixture thereof. Specifically, an alkali metal such as Li and Cs, an alkali-earth metal such as Mg, Ca and Sr, an alloy including the metal (Mg:Ag, Al:Li, Mg:In, or the like), a compound of the metal (calcium fluoride or calcium nitride), or a rare-earth metal such as Yb and Er can be used.

The electroluminescent layer 605 is composed of a signal layer or a plurality of layers. Although the embodiments described above show the figures (refer to FIGS. 1, 2, 18) in which the interface between the layers is clear, it is not always necessary to be clear. The materials forming the respective layers may be partly mixed to make the interface unclear.

In the case of this pixel shown in FIG. 3A, light emitted from the light-emitting element 603 can be extracted from the first electrode 101 side as indicated by the dashed arrow.

Then, FIG. 3B shows a cross-sectional view of a pixel where a TFT 601 is a p-channel transistor and light emitted from a light-emitting element 603 is extracted from a second electrode 102 side (in the direction of a dashed arrow). In FIG. 3B, the structures of the TFT 601, an electroluminescent layer 605, an interlayer insulating film 608, a partition 609, and the like that are provided over a substrate 600 are the same as in FIG. 3A. Therefore, description thereof will be omitted.

In FIG. 3B, in order to extract light emission to the second electrode 102 side (in the direction of the dashed arrow), the first electrode 101 is formed by using a material that reflects or blocks light or formed to have a film thickness that blocks light. Further, since the TFT 601 is a p-channel transistor, the first electrode 101 is formed by using a material that is suitable for being used as an anode. For example, a single-layer film including one or more of TiN, ZrN, Ti, W, Ni, Pt, Cr, Ag, Al and the like, a lamination layer of a titanium nitride film and a film including aluminum as its main component, and a three-layer structure of a titanium nitride film, a film including aluminum as its main component, and a titanium nitride film can be used for the first electrode 101.

In addition the first electrode 101 and a wiring that is connected to the TFT 601 can be formed by using the same material. Therefore, a process for forming the first electrode can be cut.

The second electrode 102 is formed by using a light-transmitting material or formed to have a film thickness through which light is transmitted. Further, the second electrode 102 is formed by using a material that is suitable for being used as a cathode; namely, can be formed by using a metal, alloy, or electrically conductive compound that has a smaller work function, or a mixture thereof. Specifically, an alkali metal such as Li and Cs, an alkali-earth metal such as Mg, Ca and Sr, an alloy including the metal (Mg:Ag, Al:Li, Mg:In, or the like), a compound of the metal (calcium fluoride or calcium nitride), or a rare-earth metal such as Yb and Er can be used. When this material through which light is not transmitted is used for the second electrode 102, the second electrode 102 is formed to have a film thickness (preferably, approximately 5 to 30 nm) through which light is transmitted. It is to be noted that other light-transmitting conductive oxide materials such as indium tin oxide (ITO), zinc oxide (ZnO), indium zinc oxide (IZO), and zinc oxide doped with gallium (GZO) can also be used. Alternatively, indium tin oxide containing and silicon oxide (ITSO) or ITSO (indium tin oxide containing silicon oxide) further mixed with zinc oxide (ZnO) may be used.

In the case of the pixel shown in FIG. 3B, light emitted from the light-emitting element 603 can be extracted from the second electrode 102 side as indicated by the dashed arrow.

Then, FIG. 3C shows a cross-sectional view of a pixel where a TFT 601 is a p-channel transistor and light emitted from the light-emitting element 603 is extracted from a first electrode 101 side and the second electrode 102 side (in the directions of dashed arrows). In FIG. 3C, the structures of the TFT 601, an electroluminescent layer 605, an interlayer insulating film 608, a partition 609, and the like that are provided over a substrate 600 are the same as in FIG. 3A. Therefore, description thereof will be omitted.

In FIG. 3C, in order to extract light emission to the first electrode 101 side and the second electrode 102 side (in the directions of the dashed arrows), each of the first electrode 101 and the second electrode 102 is formed by using a material that reflects or blocks light or formed to have a film thickness that blocks light (>>>a light-transmitting material or formed to have a film thickness through which light is transmitted?); namely, the first electrode 101 can be formed in the same way as the first electrode 101 shown in FIG. 3A, and the second electrode 102 can be formed in the same way as the second electrode 102 shown in FIG. 3B.

In the case of the pixel shown in FIG. 3C, light emitted from the light-emitting element 603 can be extracted from the first electrode 101 side and the second electrode 102 side as indicated by the dashed arrows.

It is to be noted that the pixel structure according to the present invention is not limited to these. For example, an n-type TFT can be used for the semiconductor element that controls current to the light-emitting element 603. In this case, it is preferable that the first electrode 101 and the second electrode 102 function as a cathode and an anode, respectively.

Further, the connecting structure of the first electrode 101 and the wiring of the TFT 601 is not limited to FIGS. 3A to 3C. For example, unlike the connecting structure shown in FIGS. 3A and 3C, the wiring of the TFT 601 may be formed after forming the first electrode 101.

The present embodiment can be freely combined with the embodiments described above.

Embodiment 7

In the present embodiment, a pixel circuit that is used for the display device described above will be described. In addition, a case of display on a digital gray scale will be exemplified.

Figure 4A:
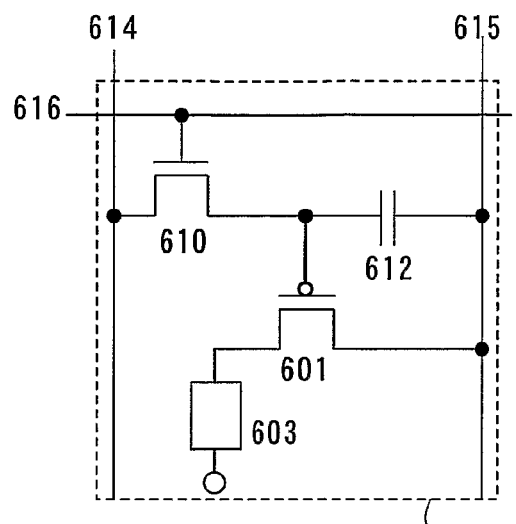
FIGS. 4A to 4C are diagrams pixel circuits according to the present invention.

FIG. 4A shows an example of an equivalent circuit diagram of a pixel 350, which includes a signal line 614, a power supply line 615, a scan line 616, and at an intersecting portion thereof, an light-emitting element 603, transistors 610 and 611 that serve as TFTs, and a capacitor 612. For the light-emitting element 603, the structure shown in the embodiment described above is used. A video signal is input to the signal line 614 by a signal line driving circuit. The transistor 610 is able to control supply of the video signal to a gate of the transistor 601 in accordance with a selection signal that is input to the scan line 616. The transistor 601 is a driving transistor that is able to control supply of current to the light-emitting element 603 in accordance with the potential of the video signal. The capacitor 612 is able to hold a voltage between the gate and source of the transistor 601. It is to be noted that, although the capacitor 612 is shown in FIG. 4A, it is not necessary that the capacitor 612 be provided when the gate capacitance of the transistor 601 or another parasitic capacitance is enough.

Figure 4B:
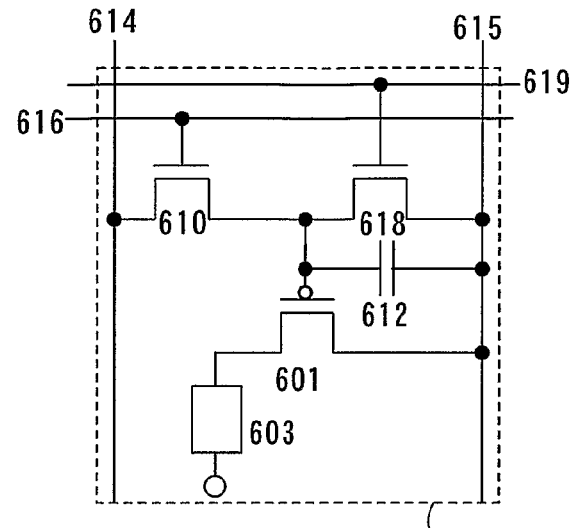

FIG. 4B is an equivalent circuit diagram of a pixel 351 where a transistor 618 and a scan line 619 are additionally provided to the pixel 350 shown in FIG. 4A. Transistor 618 makes it possible to make the potentials of the gate and source of the transistor 611 equal to each other so that a state in which no current flows into the light-emitting element 603 can be forcibly made. Therefore, the length of a sub-frame period can be made shorter than a period for inputting video signals into all pixels. Further, depending on the driving method, a state in which no current flows into the light-emitting element 603 can be forcibly made even in a pixel shown in FIG. 4A.

Figure 4C:
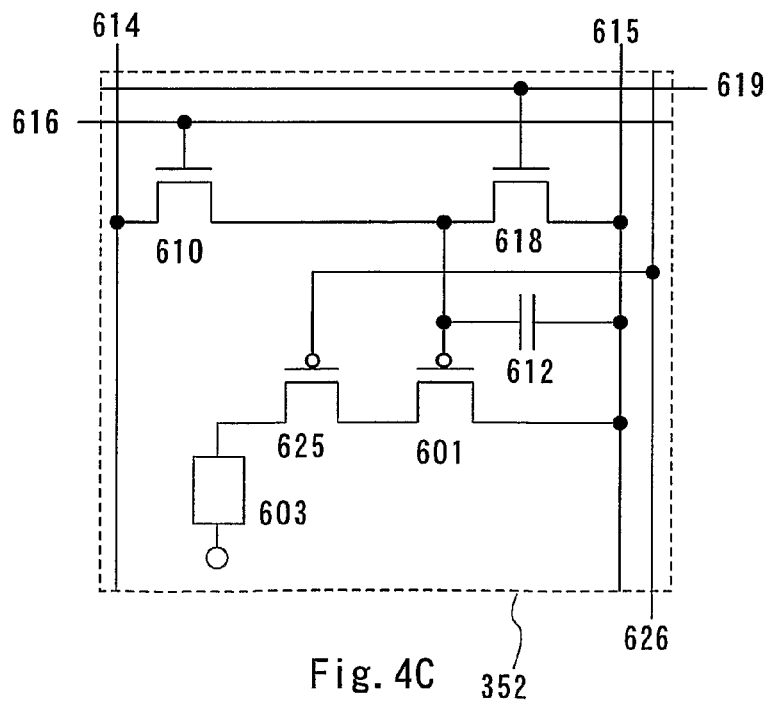

FIG. 4C is an equivalent circuit diagram of a pixel 352 where a transistor 625 and a wiring 626 are additionally provided to the pixel 351 shown in FIG. 4B. The gate of the transistor 625 has a potential fixed by the wiring 626. In addition, the transistors 601 and 625 are connected in series between the power supply line 615 and the light-emitting element 603. Therefore, in FIG. 4C, the transistor 625 is able to control the amount of current supplied to the light-emitting element 603 whereas the transistor 601 is able to control whether or not the current is supplied to the light-emitting element 603.

It is to be noted that the pixel circuit according to the present invention is not limited to the structures shown in the present embodiment, and an analog gray scale can be used besides a digital gray scale. In addition, the present embodiment can be freely combined with the embodiments described above.

Embodiment 8

In the present embodiment, the structure of a light-emitting device that has the light-emitting element described above will be described.

Figure 5:
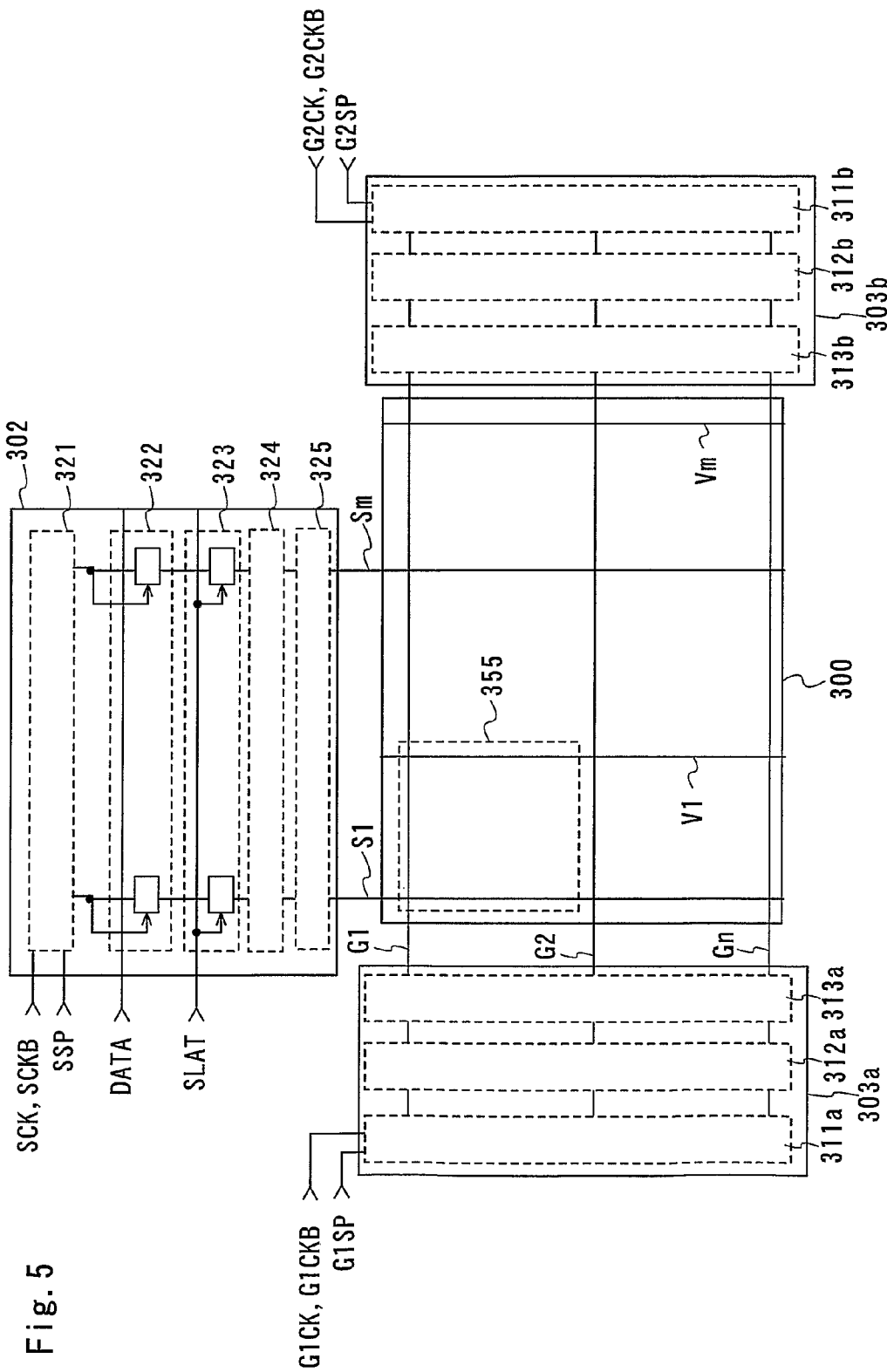
FIG. 5 is diagram illustrating a panel according to the present invention.

FIG. 5 shows a panel in which driving circuits of a signal line driving circuit 302 and a scan line driving circuit 303 are provided a around a pixel portion 300. It is to be noted that the panel indicates a state in which the pixel portion 100, the signal line driving circuit 302, and the scan line driving circuit 303 are provided over the same substrate, and also includes a state in which a FPC (flexible printed circuit) is connected thereto.

The pixel portion 300 has a plurality of pixels 355, and the light-emitting element described above is provided in each pixel. A semiconductor element (corresponding to the TFT 601 in FIGS. 4A to 4C) for controlling supply of current to the light-emitting element is connected to the light-emitting element. The cross section of the pixel including the light-emitting element is as shown in the embodiment described above. Further, the pixel 355 may have any of the equivalent circuits shown in the embodiment described above. It is to be noted that the pixel portion according to the present invention is not limited to this structure and may have a passive structure.

Two scan line driving circuit are provided with the pixel portion 300 interposed therebetween, and are a first scan line driving circuit 303a and a second scan line driving circuit 303b. It is to be noted a single scan line driving circuit or three or more scan line driving circuits may be provided. The first scan line driving circuit 303a and the second scan line driving circuit 303b have circuits that serve as shift registers 311a and 311b, level shifters 312a and 312b, and buffers 313a and 313b, respectively. Signals such as first and second gate start pulses (G1SP and G2SP), first and second gate clock signals (G1CK and G2CK), and signals obtained by inverting the clock signals (G1CKB and G2CKB) are input to the shift resisters 311a and 311b, respectively.

Scan lines (G1 to Gn) are connected to the first and second scan line driving circuit 303a and 303b, from which signals are supplied to each pixel 355 provided in the pixel portion 300. A semiconductor element (corresponding to the transistor 610 in FIGS. 4A to 4C) for selecting each pixel is connected to each scan line, and is selected when an image signal is written in the pixel.

Further, the signal line driving circuit 302 has circuits that serve as a shift register 321, a first latch 322, a second latch 323, a level shifter 324, and a buffer 325. Signals such as a start pulse (SSP), data (DATA) such as a video signal, and signals such as a latch (LAT) signal are input to the shift register 321, the first latch 322, and the second latch 323, respectively. Signal lines (S1 to Sm) are connected to the signal line driving circuit 303a and 303b, from which image signals are supplied to each pixel 355 provided in the pixel portion 300.

These signal line driving circuit 302, scan line driving circuit 303, and pixel portion 300 can be formed by using semiconductor elements provided over the same substrate, for example, can be formed by using thin film transistors provided over a glass substrate.

Next, the cross-sectional structure of the panel shown in FIG. 5 will be described with reference to FIGS. 6A and 6B.

FIG. 6A shows enlarged views of cross sections of the first scan line driving circuit 303a, second scan line driving circuit 303b, and pixel portion 300 provided over a substrate 600. In the pixel portion 300, a TFT 601 that controls supply of current to a light-emitting element 603 and a capacitor 612 are provided. It is to be noted that the capacitor 612 can function with a structure of an insulator provided between a pair of conductors, and a conductor composed of the same layer as a gate electrode, an insulator composed of an interlayer insulating film 608, a gate insulating film, and a conductor composed of the same layer as a wiring of the TFT constitute the capacitor 612 in the present embodiment. However, the capacitor 612 is not to be considered limited to this structure.

It is to be noted that the structures of the light-emitting element 603 and the TFT 601 can be combined with the structures shown in Embodiment 5.

The first and second scan line driving circuits 303a and 303b have CMOS circuits 630a and 630b composed of thin film transistors, respectively. Since the buffers 313a and 313b of the respective scan line driving circuits are simpler as compared to the other circuits, the CMOS circuits 630a and 630b can be applied. Of course, the CMOS circuits 630a and 630b may be applied to the other circuits.

In addition, although not shown in FIG. 6A, the CMOS circuits 630a and 630b can be applied to the circuits of the signal line driving circuit 302.

Further, an opposed substrate 650 is attached with a sealing material 651. Known materials such as an epoxy resin can be used for the sealing material 651. In FIG. 6A, the sealing material 651 is provided to cover a portion of the scan line driving circuit. Accordingly, the frame of the panel can be narrower.

As a result of the attachment, a space is formed between the substrate 600 and the opposed substrate 650. Since the light-emitting element 603 is deteriorated due to air and water, the space is preferably filled with an inert gas such as nitrogen, or may be filled with a resin or the like. Further, in order to keep the gap, a spacer may be disposed. The spacer may have a function as a drying agent.

Outside the sealing material 651, a connecting terminal 652 for inputting signals to the first and second scan line driving circuits 303a and 303b is provided. The connecting terminal 652 is connected to an FPC through an anisotropic conductive film.

Although the opposed substrate 650 is attached with the sealing material 651 in FIG. 6A, a resin that is used for filling the space can be used for the attachment.

Further, FIG. 6B shows a cross-sectional view for the case of providing a black matrix 655 and a color filter 656 on an opposed substrate 650. The color filter 656 is provided to be located above at least a light-emitting element 603.

The black matrix 655 is provided to be located above wirings such as the scan lines (G1 to Gn), signal lines (S1 to Sm), or power supply lines (V1 to Vm). Further, the black matrix 655 may be provided over the first and second scan line driving circuits 303a and 303b. Since the other structure is the same as the structure shown in FIG. 6A, description there of is omitted.

Although a case of using the color filter 656 is shown as an example in FIG. 6B, a color conversion layer may be further combined.

In addition, although the color filter 656 is provided on the opposed substrate 650 side in FIG. 6B, a color filter may be provided on the substrate 600 side. For example, a color filter may be formed on the back side of the substrate 600 or over a second electrode 102.

Similarly, it is not always necessary to provide the black matrix 655 on the opposed substrate 650 side, and the black matrix 655 may be provided on the substrate 600 side. Alternatively, a black pigment mixed in an interlayer insulating film 608 can be function as a black matrix.

It is to be noted that a structure of a lower-concentration impurity region overlapped with a gate electrode in a thin film transistor, a so-called GOLD (Gate Overlapped LDD) structure is shown as an example in FIGS. 6A and 6B. In addition, a structure of a lower-concentration impurity region that is not overlapped with a gate electrode, a so-called LDD (Lightly Doped Drain) structure may be used.

Although the panel that has the scan line driving circuit and signal line driving circuit provided together with the pixel portion 300 on the same substrate is shown as an example in the present embodiment, the present invention is note limited to this. For example, each driving circuit may be formed by using an IC chip. In this case, the IC chip can be mounted on a substrate by a COG method or a TAB method.

The present embodiment can be freely combined with the embodiments described above.

Embodiment 9

Electronic devices provided with a light-emitting device according to the present invention include a television set (also, simply referred to as a TV or a television receiver), a digital camera, a digital video camera, a cellular phone unit (also, simply referred to as a mobile-phone unit or a cellular phone), a mobile information terminal such as PDA, a portable game machine, a monitor for a computer, a computer, a sound reproduction device such as a in-car audio system, an image reproduction device provided with a recording medium such as a home-use game machine, and the like. Specific examples thereof will be described with reference to FIGS. 7A to 7F.

Figure 7A:
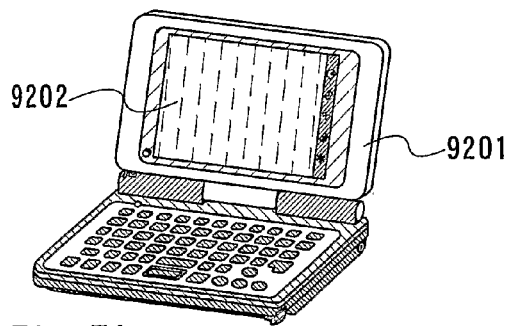
FIGS. 7A to 7F are diagrams illustrating electronic devices according to the present invention.

A mobile terminal device shown in FIG. 7A includes a main body 9201, a display portion 9202, and the like. A light-emitting device according to the present invention can be applied to the display portion 9202. Accordingly, it is possible to provide a mobile terminal device achieving lower power consumption without increasing the driving voltage even when a light-emitting element is made thicker. Further, the yield of the mobile terminal device is improved since the light-emitting element can be made thicker.

Figure 7B:
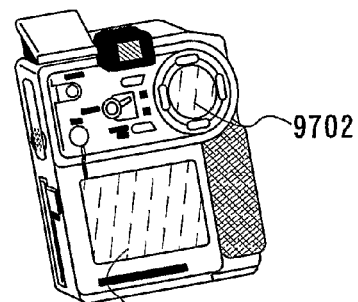

A digital video camera shown in FIG. 7B includes a display portion 9701, a display portion 9702, and the like. A light-emitting device according to the present invention can be applied to the display portion 9701. Accordingly, it is possible to provide a digital video camera achieving lower power consumption without increasing the driving voltage even when a light-emitting element is made thicker. Further, the yield of the digital video camera is improved since the light-emitting element can be made thicker.

Figure 7C:
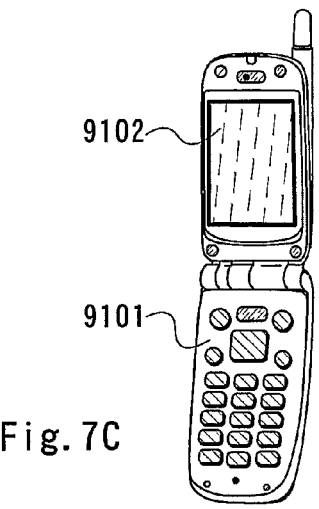

A cellular phone shown in FIG. 7C includes a main body 9101, a display portion 9102, and the like. A light-emitting device according to the present invention can be applied to the display portion 9102. Accordingly, it is possible to provide a cellular phone achieving lower power consumption without increasing the driving voltage even when a light-emitting element is made thicker. Further, the yield of the cellular phone is improved since the light-emitting element can be made thicker.

Figure 7D:
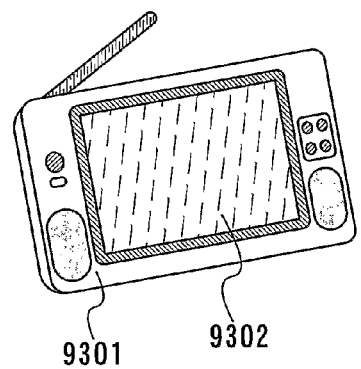

A portable television set shown in FIG. 7D includes a main body 9301, a display portion 9302, and the like. A light-emitting device according to the present invention can be applied to the display portion 9302. Accordingly, it is possible to provide a portable television set achieving lower power consumption without increasing the driving voltage even when a light-emitting element is made thicker. Further, the yield of the portable television set is improved since the light-emitting element can be made thicker. In addition, the light-emitting device according to the present invention can be applied to various types of television sets such as a small-sized television incorporated in a mobile terminal such as a cellular phone handset, a medium-sized television that is portable, and a large-sized television (for example, 40 inches in size or more).

Figure 7E:
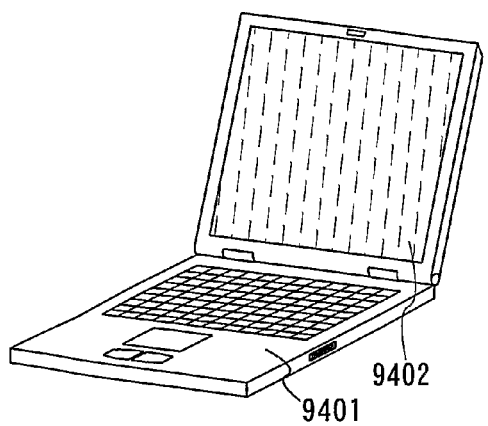

A portable computer shown in FIG. 7E includes a main body 9401, a display portion 9402, and the like. A light-emitting device according to the present invention can be applied to the display portion 9402. Accordingly, it is possible to provide a portable computer achieving lower power consumption without increasing the driving voltage even when a light-emitting element is made thicker. Further, the yield of the portable computer is improved since the light-emitting element can be made thicker.

Figure 7F:
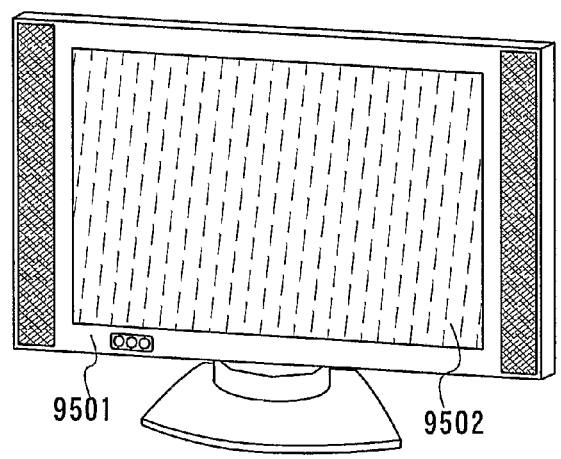

A television set shown in FIG. 7F includes a main body 9501, a display portion 9502, and the like. A light-emitting device according to the present invention can applied to the display portion 9502. Accordingly, it is possible to provide a television set achieving lower power consumption without increasing the driving voltage even when a light-emitting element is made thicker. Further, the yield of the television set is improved since the light-emitting element can be made thicker.

As described above, according to the present invention, it is possible to provide an electronic device achieving lower power consumption without increasing the driving voltage even when a light-emitting element is made thicker.

EXAMPLES

Example 1

Figure 8:
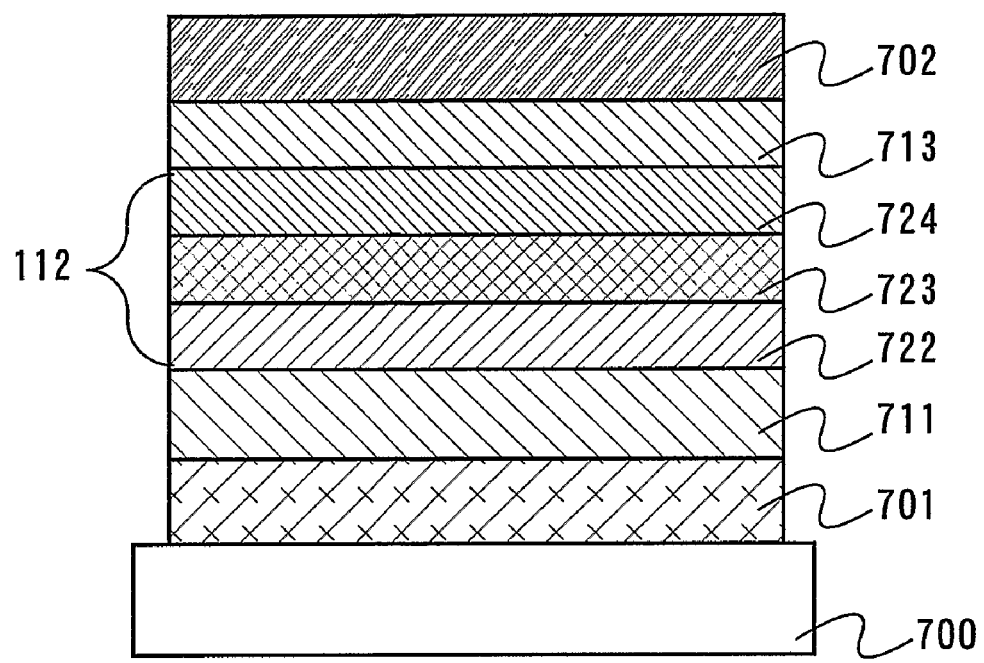
FIG. 8 is a diagram showing illustrating a light-emitting element according to the present invention.

In the present example, a light-emitting element manufactured by using a layer in which an organic compound and an inorganic compound are mixed for a layer that generates holes will be described with reference to FIG. 8.

Indium tin oxide containing silicon was deposited over a glass substrate 700 by sputtering to form a first electrode 701 so as to have a thickness of 110 nm.

Then, DNTPD, a molybdenum oxide, and rubrene were deposited over the first electrode 701 by evaporation in vacuum to form a layer 711 composed of the DNTPD, the molybdenum oxide, and the rubrene so as to have a thickness of 120 nm. The mass ratio of the DNTPD, the molybdenum oxide, and the rubrene was made to be 1:0.5:0.02.

Then, NPB was deposited over the layer 711 composed of the DNTPD, the molybdenum oxide, and the rubrene by evaporation in vacuum to form a second layer 722 composed of the NPB so as to have a thickness of 10 nm.

Then, $Alq_3$ and coumarin 6 were deposited over the layer 722 composed of the NPB by co-evaporation in vacuum to form a layer 723 including the $Alq_3$ and the coumarin 6. It is to be noted that the coumarin 6 was made to be included at 0.01 percent by mass to the $Alq_3$. Accordingly, the coumarin 6 was dispersed in the $Alq_3$. Further, the thickness of the layer 723 was made to be 37.5 nm.

Then, $Alq_3$ was deposited over the layer 723 including the $Alq_3$ and the coumarin 6 by evaporation in vacuum to form a layer 724 composed of the $Alq_3$ so as to have a thickness of 37.5 nm.

Then, lithium fluoride was deposited over the layer 724 composed of the $Alq_3$ by evaporation in vacuum to form a layer 713 composed of the lithium fluoride so as to have a thickness of 1 nm.

Then, aluminum was deposited over the layer 713 compose of the lithium fluoride by evaporation in vacuum to form a second electrode 702 so as to have a thickness of 200 nm.

When a voltage is applied to the first electrode 701 and the second electrode 702 in the thus manufactures light-emitting element to pass an electric current, the coumarin 6 produces luminescence.

In this case, the first electrode 701 serves as an anode whereas the second electrode 702 serves as a cathode. Further, the layer 711 composed of the DNTPD, the layer 722 composed of the NPB, the layer 723 including the $Alq_3$ and the coumarin 6, the layer 724 composed of the $Alq_3$, and the layer 713 compose of the lithium fluoride serve as a layer that generates holes, a hole transporting layer, a light-emitting layer, an electron transporting layer, and a layer that generates electrons, respectively.

Figure 9:
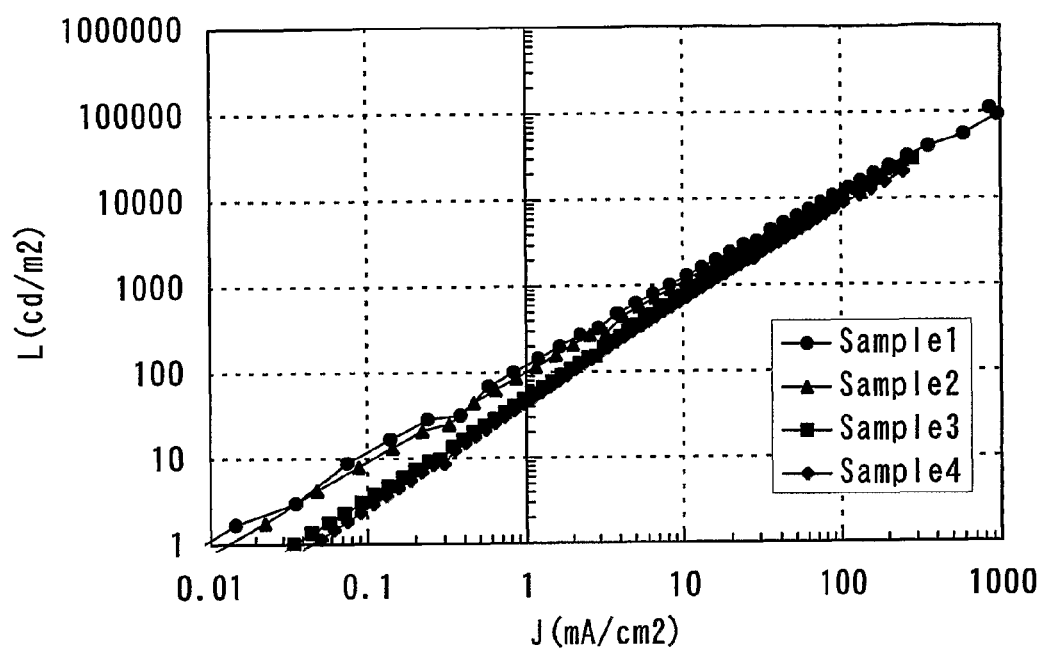
FIG. 9 is a diagram showing current density-luminance characteristics of a light-emitting element according to the present invention.
Figure 10:
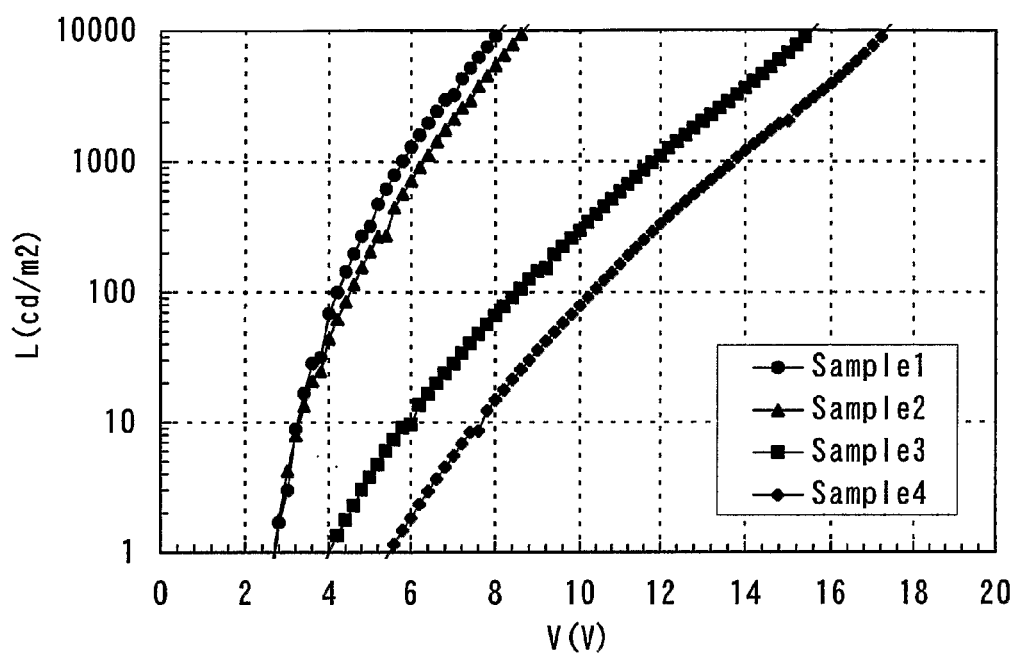
FIG. 10 is a diagram showing voltage-luminance characteristics of the light-emitting element according to the present invention.
Figure 11:
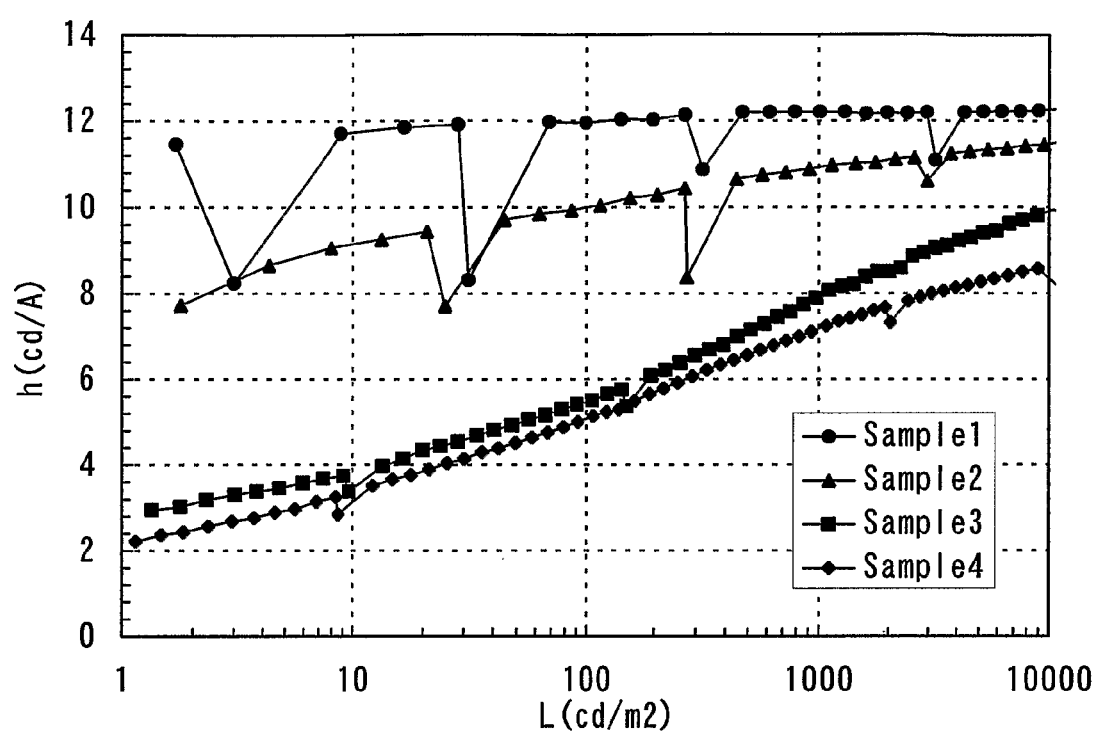
FIG. 11 is a diagram showing luminance-current efficiency characteristics of the light-emitting element according to the present invention.

FIG. 9 shows current density-luminance characteristics for the case of keeping the light-emitting element according to the present example at 105° C. FIG. 10 shows voltage-luminance characteristics thereof. FIG. 11 shows luminance-current efficiency characteristics thereof. In FIG. 9, the horizontal axis indicates current density whereas the vertical axis indicates luminance. In FIG. 10, the horizontal axis indicates voltage whereas the vertical axis indicates luminance. In FIG. 11, the horizontal axis indicates luminance whereas the vertical axis indicates current efficiency. It is to be noted that the respective characteristics were measured in the initial condition (Sample 1), after a lapse of 30 hours (Sample 2), after a lapse of 154 hours (Sample 3), and after a lapse of 462 hours (Sample 4).

Figure 12:
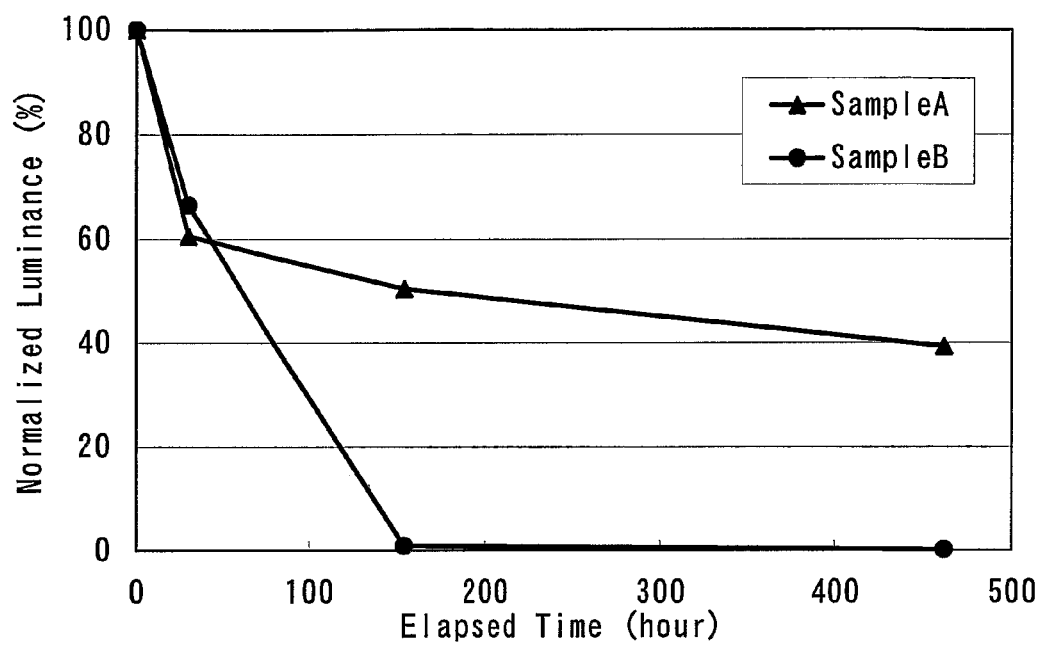
FIG. 12 is a diagram showing deterioration of the light-emitting element according to the present invention.

Based on these results, deterioration (normalized evaluation) with elapsed time on applying 7 V is shown (refer to FIG. 12). In addition, FIG. 12 shows a result of the sample according to the present invention (Sample A) together with a result of a comparative sample (Sample B) using a layer composed of DNTPD and rubrene for the layer 711 that generates holes.

It is determined from FIG. 12 that Sample A is less deteriorated with time than Sample B. Accordingly, a stable light-emitting element can be obtained by using a layer in which a molybdenum oxide is mixed for a layer that generates holes.

As described above, an effect of reduced deterioration with time can be achieved when DNTPD is used for the organic compound. Since the glass-transition temperature of DNTPD is 94° C., the glass-transition temperature according to the present invention is 80° C. or more, preferably 90° C. or more and 300° C. or less, considering the glass-transition temperature of DNTPD.

Example 2

Synthesis Example

A synthesis method of the benzidine derivative represented by the structure formula (2) will be described.

[Step 1]

A synthesis method of 2-bromo-spiro-9,9'-bifluorene will be described.

In a 100 mL three neck flask, 1.26 g (0.052 mol) of magnesium was put, vacuum was formed in the system, and stirring on heating was carried out for 30 minutes activate magnesium. After cooling to room temperature, a nitrogen gas stream was formed in the system. Then, 5 ml of diethyl ether and a few drops of dibromoethane were added, and 11.65 g of 2-bromobiphenyl (0.050 mol) dissolved in 15 ml of diethyl ether was slowly dropped. After dropping, the reaction was refluxed for 3 hours to provide a Grignard reagent. In a 200 mL three neck flask, 11.7 g of 2-bromofluorenone (0.045 mol) and 40 ml of diethyl ether were put. The synthesized Grignard reagent was slowly dropped into this reaction solution. After the dropping, the solution was refluxed for 2 hours and stirred at room temperature overnight (15 hours). After reaction, the reaction solution was washed twice with a saturated ammonium chloride solution, and the water layer was extracted twice with ethyl acetate, mixed with the organic layer, and washed twice with a saturated salt solution. After drying with magnesium sulfate, suction filtration and condensation were performed to obtain 18.76 g of solid 9-(2-biphenylyl)-2-bromo-9-fluorenol at a yield of 90%.

Next, in a 200 mL three neck flask, 18.76 g (0.045 mol) of the synthesized 9-(2-biphenylyl)-2-bromo-9-fluorenol and 100 mL of glacial acetic acid were, and a few drops of concentrated hydrochloric acid were put and refluxed for 2 hours. After reaction, precipitation was collected by suction filtration, and washed with saturated sodium hydrogencarbonate and water on filtrating. An obtained brown solid was recrystallized with ethanol to obtain 10.24 g of a light-brown powdery solid at a yield of 57%. Nuclear magnetic resonance analysis (NMR) confirmed that this light-brown powdery solid is 2-bromo-spiro-9,9'-bifluorene. The $^1$H-NMR is as follows.

Here is the $^1$H-NMR of this compound.

$^1$H-NMR (300 MHz, $CDCl_3$) δ ppm: 7.86-7.79 (m, 3H), 7.70 (d, 1H, J=8.4 Hz), 7.47-7.50 (m, 1H), 7.41-7.34 (m, 3H), 7.12 (t, 3H, J=7.7 Hz), 6.85 (d, 1H, J=2.1 Hz), 6.74-6.70 (m, 3H)

Further, here is a synthesis scheme (b-1) of the synthesis method described above.

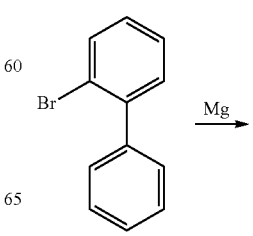

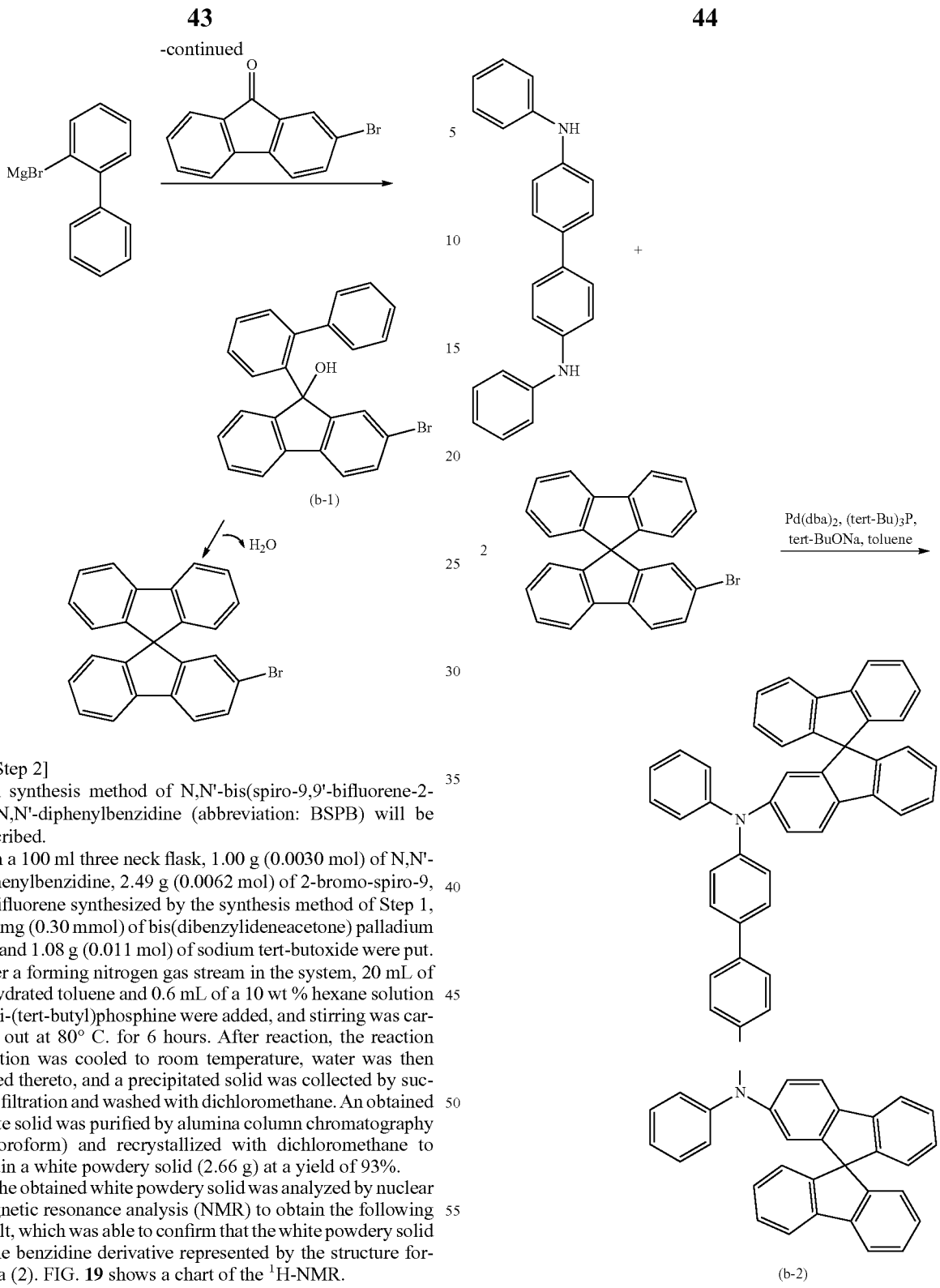

[Step 2]
A synthesis method of N,N'-bis(spiro-9,9'-bifluorene-2-yl)-N,N'-diphenylbenzidine (abbreviation: BSPB) will be described.

In a 100 ml three neck flask, 1.00 g (0.0030 mol) of N,N'-diphenylbenzidine, 2.49 g (0.0062 mol) of 2-bromo-spiro-9,9'-bifluorene synthesized by the synthesis method of Step 1, 170 mg (0.30 mmol) of bis(dibenzylideneacetone) palladium (0), and 1.08 g (0.011 mol) of sodium tert-butoxide were put. After a forming nitrogen gas stream in the system, 20 mL of dehydrated toluene and 0.6 mL of a 10 wt % hexane solution of tri-(tert-butyl)phosphine were added, and stirring was carried out at 80° C. for 6 hours. After reaction, the reaction solution was cooled to room temperature, water was then added thereto, and a precipitated solid was collected by suction filtration and washed with dichloromethane. An obtained white solid was purified by alumina column chromatography (chloroform) and recrystallized with dichloromethane to obtain a white powdery solid (2.66 g) at a yield of 93%.

Figure 19:
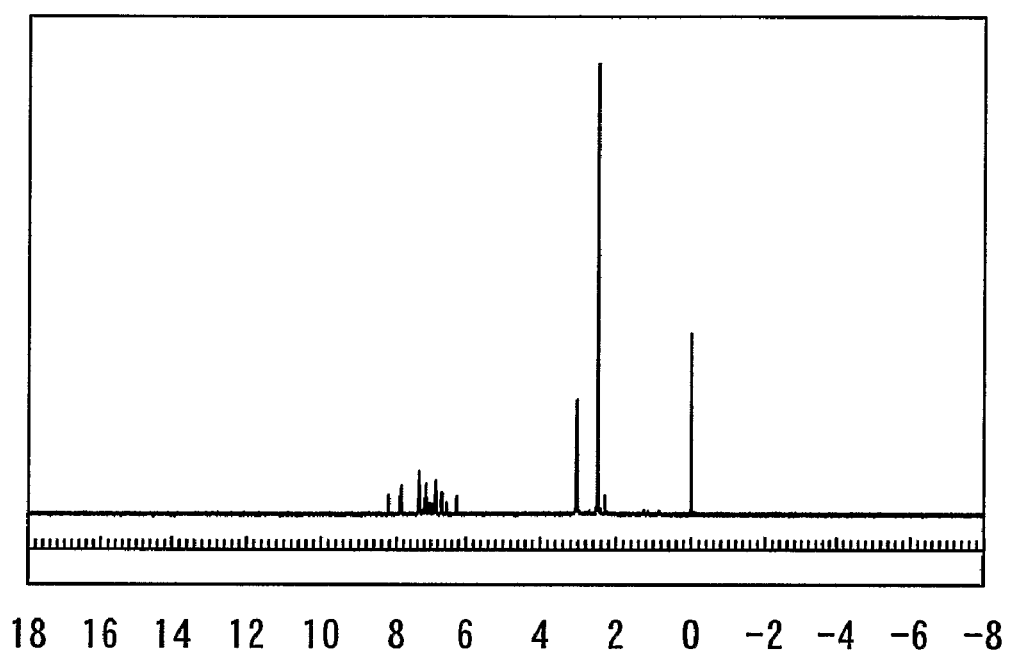
FIG. 19 is a diagram showing a result of analyzing a white powdery solid synthesized in accordance with Step 2 of Example 2 by nuclear magnetic resonance.

The obtained white powdery solid was analyzed by nuclear magnetic resonance analysis (NMR) to obtain the following result, which was able to confirm that the white powdery solid is the benzidine derivative represented by the structure formula (2). FIG. 19 shows a chart of the $^1$H-NMR.

$^1$H-NMR (300 MHz, DMSO-$d_6$) δ ppm: 7.93-7.89 (m, 8H), 7.39-7.33 (m, 10H), 7.19-7.14 (m, 8H), 7.09-6.96 (m, 6H), 6.89-6.84 (m, 8H), 6.69 (d, 4H, J=7.5 Hz), 6.54 (d, 2H, J=7.8 Hz), 6.25 (d, 2H, J=2.4 Hz)

Here is a synthesis scheme (b-2) of the synthesis method described above. As described above, the compound according to the present invention can be synthesized by a coupling reaction of N,N'-diphenylbenzidine and 2-bromo-spiro-9,9'-bifluorene.

Figure 17:
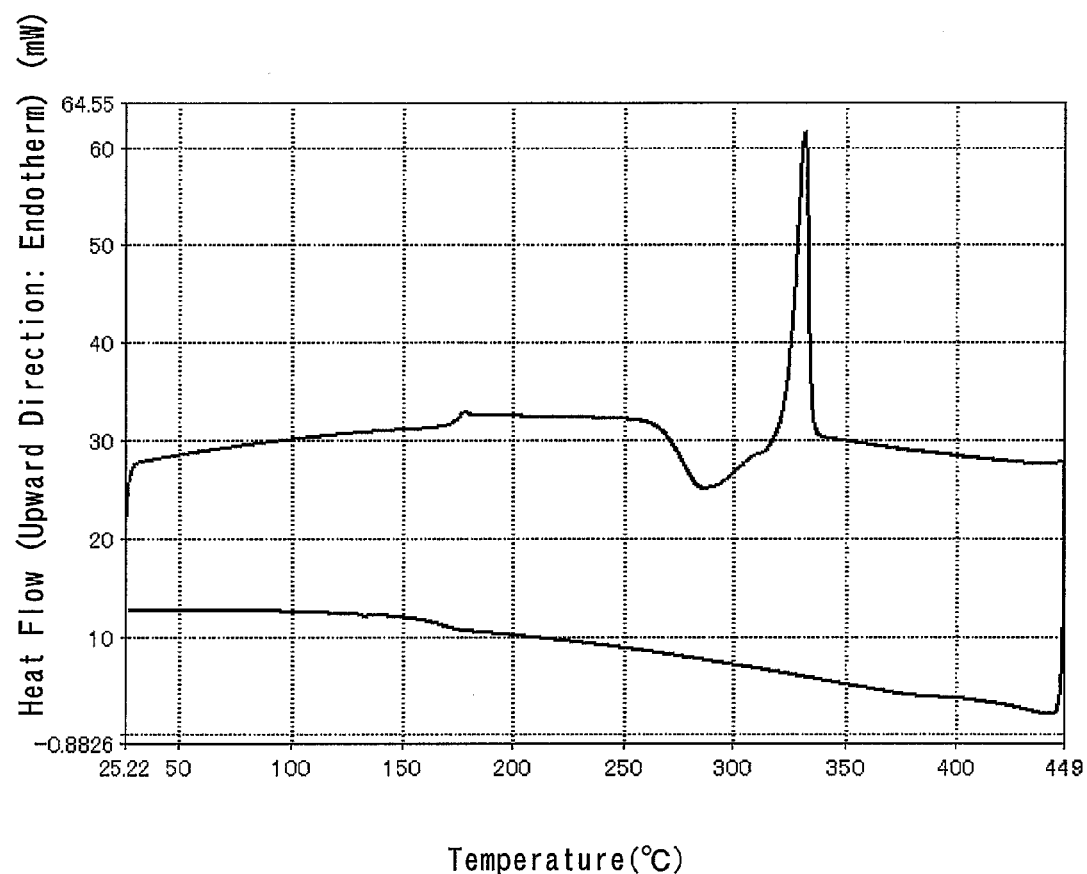
FIG. 17 is a measurement result of analyzing a benzidine derivative according to the present invention by differential scanning calorimetry.

Further, the glass-transition temperature, crystallization temperature, and melting point of the obtained compound were obtained by a differential scanning calorimeter (DSC) manufactured by PerkinElmer, Inc. under model number Pyrisl DSC. The measurement by the DSC here was carried out in accordance with the following procedure. First, a sample (obtained compound) was heated to 450° C. at a heating rate of 40° C./min and then cooled at a cooling rate of 40° C./min to make the sample in a glass state. Then, the sample in the glass state sample was heated at a heating rate of 10° C./min. Hence, the measurement result shown in FIG. 17 was obtained. In FIG. 17, the horizontal axis indicates temperature (° C.) whereas the vertical axis indicates heat flow (the upward direction indicates endotherm) (mW). From the measurement result, it is determined that the glass-transition temperature and crystallization temperature of the obtained compound are 172° C. and 268° C., respectively. Further, it is determined that the melting point is 323° C. or more and 324° C. or less from the intersection of a tangential line at 312° C. with a tangential line at a temperature of 327° C. or more and 328° C. or less. Accordingly, it is determined that the glass-transition temperature of the BSPB synthesized in the present example meets the range of 150° C. or more, preferably 160° C. or more and 300° C. or less, and that the BSPB has a melting point in the range of 180° C. or more and 400° C. or less.

The obtained compound (4.74 g) was sublimed and purified under the condition of 14 Pa and 350° C. for 24 hours to collect 3.49 g compound at a collection rate of 74%.

As described above, the obtained compound has a high glass-transition temperature of 172° C. and has favorable heat resistance. Further, the peak that indicates crystallization of the obtained compound is broad in FIG. 17, and it is thus determined that the obtained compound is not likely to be crystallized.

Example 3

A light-emitting element manufactured by using a compound (hereinafter, simply referred to as BSPB) that has a glass-transition temperature of 172° C., obtained by the synthesis described in Step 2 of the example described above, will be described with reference to FIG. 8.

Indium tin oxide containing silicon was deposited over a glass substrate 700 by sputtering to form a first electrode 701 so as to have a thickness of 110 nm.

Then, BSPB, a molybdenum oxide, and rubrene were deposited over the first electrode 701 by evaporation in vacuum to form a layer 711 composed of the BSPB, the molybdenum oxide, and the rubrene so as to have a thickness of 120 nm. The mass ratio of the BSPB, the molybdenum oxide, and the rubrene was made to be 2:0.75:0.04.

Then, NPB was deposited over the layer 711 composed of the BSPB, the molybdenum oxide, and the rubrene by evaporation in vacuum to form a second layer 722 composed of the NPB so as to have a thickness of 10 nm.

Then, $Alq_3$ and coumarin 6 were deposited over the layer 722 composed of the NPB by co-evaporation in vacuum to form a layer 723 including the $Alq_3$ and the coumarin 6. It is to be noted that the coumarin 6 was made to be included at 0.01 percent by mass to the $Alq_3$. Accordingly, the coumarin 6 was dispersed in the $Alq_3$. Further, the thickness of the layer 723 was made to be 37.5 nm.

Then, $Alq_3$ was deposited over the layer 723 including the $Alq_3$ and the coumarin 6 by evaporation in vacuum to form a layer 724 composed of the $Alq_3$ so as to have a thickness of 37.5 nm.

Then, lithium fluoride was deposited over the layer 724 composed of the $Alq_3$ by evaporation in vacuum to form a layer 713 composed of the lithium fluoride so as to have a thickness of 1 nm.

Then, aluminum was deposited over the layer 713 composed of the lithium fluoride by evaporation in vacuum to form a second electrode 702 so as to have a thickness of 200 nm.

When a voltage is applied to the first electrode 701 and the second electrode 702 in the thus manufactured light-emitting element to pass an electric current, the coumarin 6 produces luminescence.

In this case, the first-electrode 701 serves as an anode whereas the second electrode 702 serves as a cathode. Further, the layer 711 composed of the BSPB, the layer 722 composed of the NPB, the layer 723 including the $Alq_3$ and the coumarin 6, the layer 724 composed of the $Alq_3$, and the layer 713 composed of the lithium fluoride serve as a layer that generates holes, a hole transporting layer, a light-emitting layer, an electron transporting layer, and a layer that generates electrons, respectively.

Figure 13:
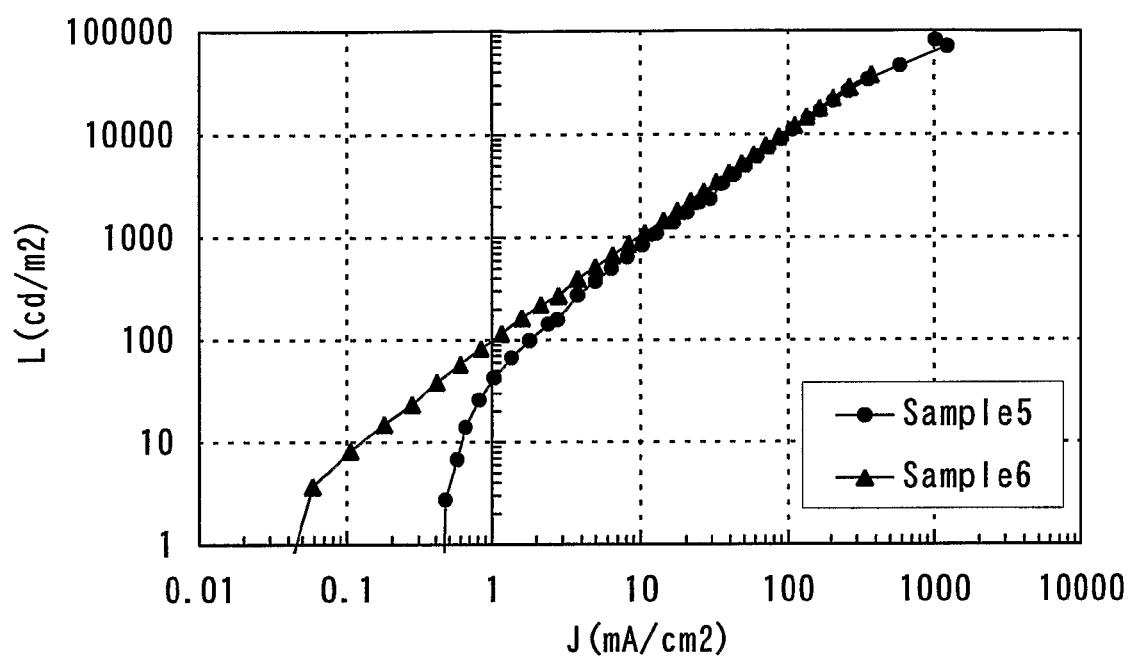
FIG. 13 is a diagram showing current density-luminance characteristics of a light-emitting element according to the present invention.
Figure 14:
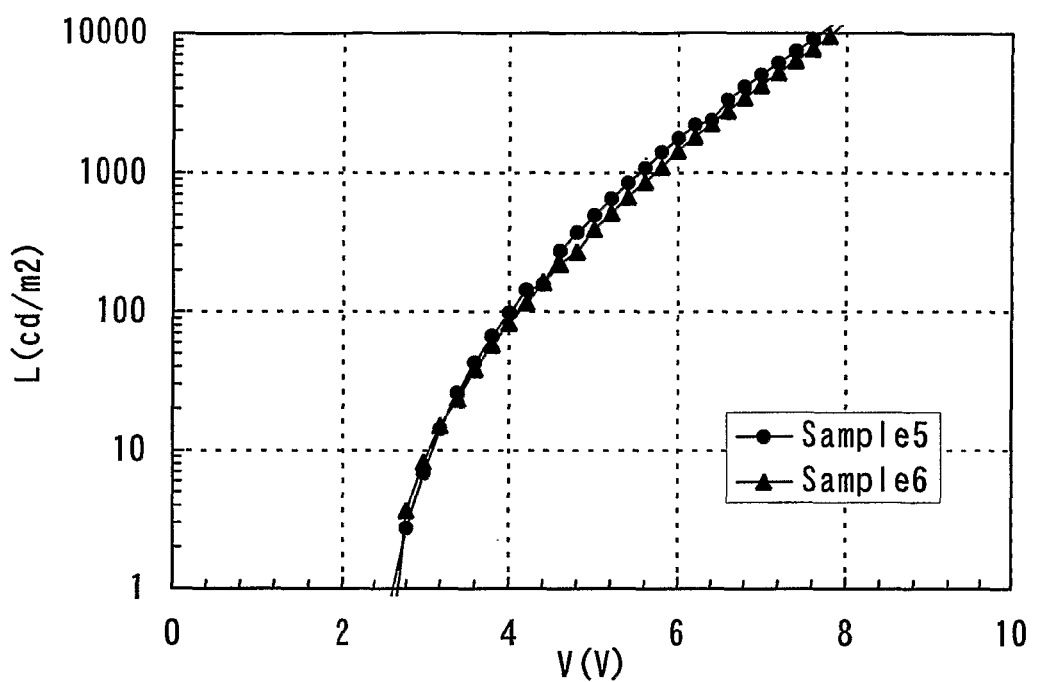
FIG. 14 is a diagram showing voltage-luminance characteristics of the light-emitting element according to the present invention.
Figure 15:
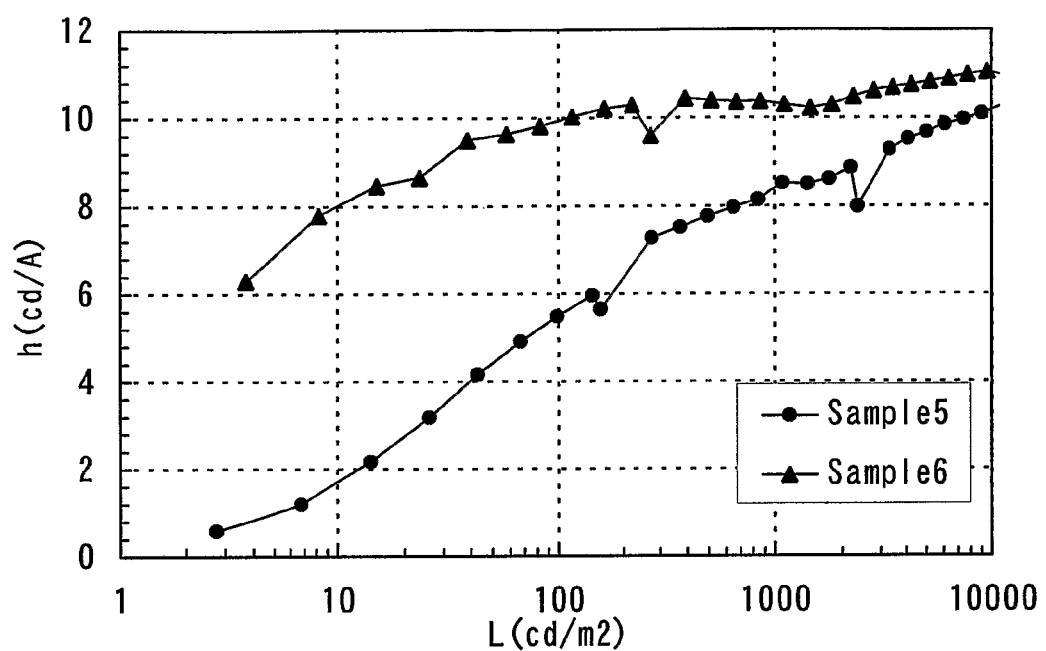
FIG. 15 is a diagram showing luminance-current efficiency characteristics of the light-emitting element according to the present invention.

FIG. 13 shows current density-luminance characteristics for the case of keeping the light-emitting element according to the present example at 105° C. FIG. 14 shows voltage-luminance characteristics thereof. FIG. 15 shows luminance-current efficiency characteristics thereof. In FIG. 13, the horizontal axis indicates current density whereas the vertical axis indicates luminance. In FIG. 14, the horizontal axis indicates voltage whereas the vertical axis indicates luminance. In FIG. 15, the horizontal axis indicates luminance whereas the vertical axis indicates current efficiency. It is to be noted that the respective characteristics were measured in the initial condition (Sample 5) and after a lapse of 30 hours (Sample 6).

Figure 16:
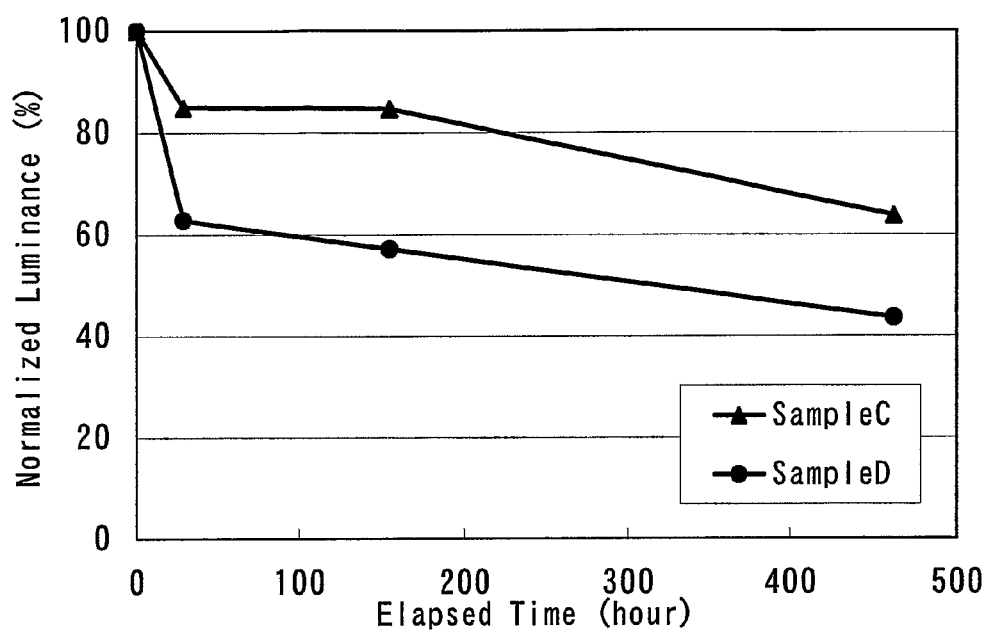
FIG. 16 is a diagram showing deterioration of the light-emitting element according to the present invention.

Based on these results, deterioration (normalized evaluation) with elapsed time on applying 7 V is shown (refer to FIG. 16). In addition, FIG. 16 shows a result of the sample according to the present invention (Sample C) together with a result of a comparative sample (Sample D) using a layer composed of BSPB and rubrene for the layer 711 that generates holes.

It is determined from FIG. 16 that Sample C is less deteriorated with time than Sample D. Accordingly, a stable light-emitting element can be obtained by using a layer in which a molybdenum oxide is mixed for a layer that generates holes.

Further, it is determined that Sample C is less deteriorated with time than Sample A. As described above, a thermally stable and highly heat-resistant light-emitting element can be obtained by using a layer in which BSPB that has a higher glass-transition temperature and a higher melting point and a molybdenum oxide are mixed. Further, even when this layer is made thicker, a light-emitting element without increase in driving voltage can be obtained.

Example 4

In the present example, the measurement result of voltage-current characteristics of a light-emitting element including a layer in which an organic compound and an inorganic compound are mixed, and the result of a constant-current driving test for the light-emitting element are shown.

First, BSPB (film thickness: 50 nm), NPB (film thickness; 10 nm), a mixed layer (film thickness: 37.5 nm) of Alq$_3$ and coumarin 6 (mixing ratio (molar ratio) of Alq$_3$ and coumarin 6=1:0.01), Alq$_3$ (film thickness: 37.5 nm), LiF (film thickness: 1 nm), and Al (film thickness: 200 nm) were stacked in order as a light-emitting element including no layer in which an organic compound and an inorganic compound are mixed (Sample 8).

In addition, mixed layer (film thickness: 120 nm) of BSPB, an molybdenum oxide, and rubrene (mixing ratio (molar ratio) of BSPB, the molybdenum oxide, and rubrene=2:0.75: 0.04), NPB (film thickness; 10 nm), a mixed layer (film thickness: 37.5 nm) of Alq$_3$ and coumarin 6 (mixing ratio (molar ratio) of Alq$_3$ and coumarin 6=1:0.01), Alq$_3$ (film thickness: 37.5 nm), LiF (film thickness: 1 nm), and Al (film thickness: 200 nm) were stacked in order as a light-emitting element including a layer in which an organic compound and an inorganic compound are mixed (Sample 9).

Figure 20:
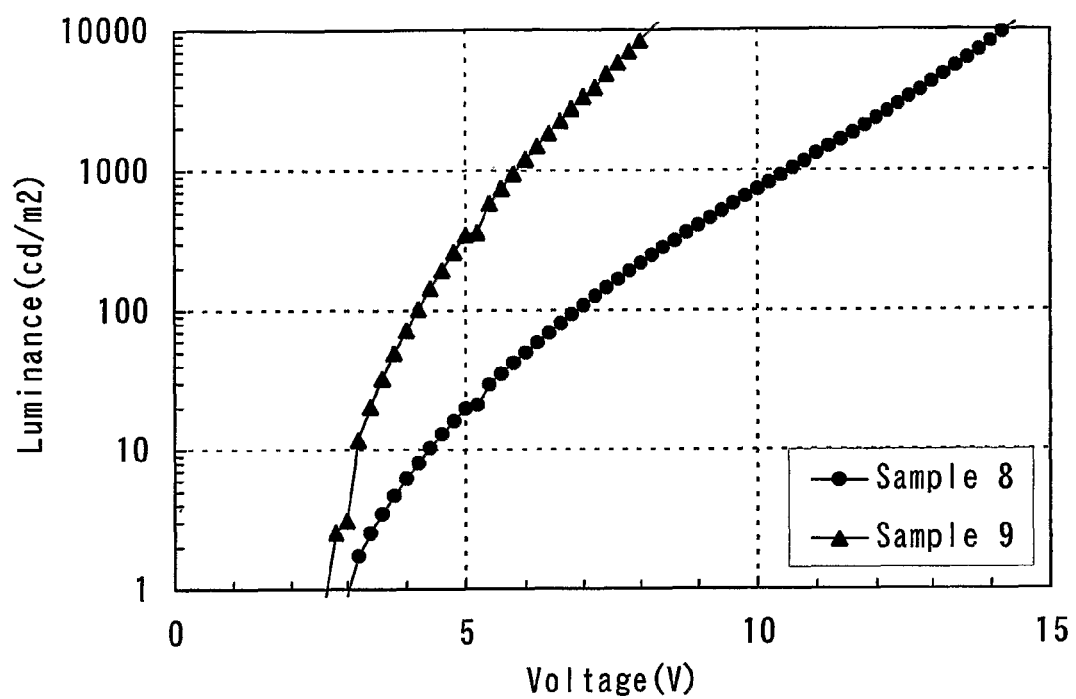
FIG. 20 is a diagram showing voltage-luminance characteristics of a light-emitting element according to the present invention.

FIG. 20 shows voltage-luminance (cd/m$^2$) characteristics of Samples 8 and 9. It is determined that the voltage for obtaining the same luminance, that is, the driving voltage, is lower in the case of Sample 9 including the molybdenum oxide.

Figure 21:
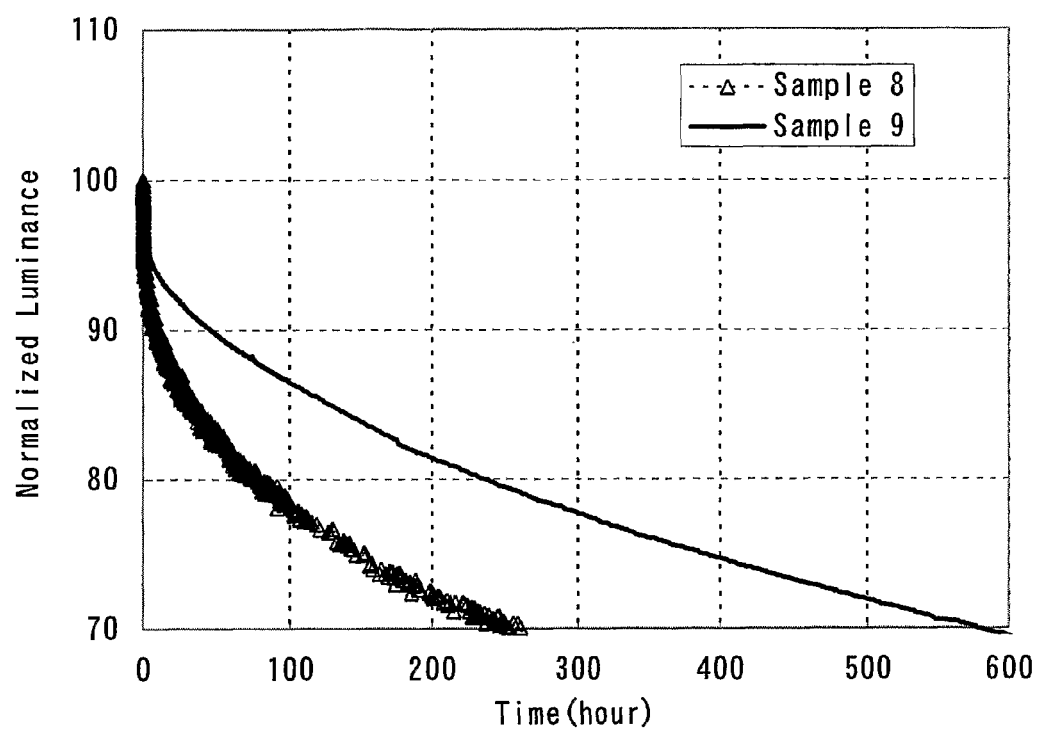
FIG. 21 is a diagram showing the result of a constant-current driving test for a light-emitting element according to the present invention.

Next, FIG. 21 shows the result of a constant-current driving test (initial luminance: 3000 cd/m$^2$) for Samples 8 and 9. It is determined that Sample 9 including the molybdenum oxide deteriorates at a slower rate and has higher reliability.

Although the present invention has been fully described by way of example with reference to the accompanying drawings, it is to be understood that various changes and modifications will be apparent to those skilled in the art. Therefore, unless such changes and modifications depart from the scope of the present invention hereinafter defined, they should be construed as being included therein.

The invention claimed is:
1. A light-emitting element comprising:
a pair of electrodes; and
a first layer formed between the pair of electrodes,
wherein the first layer comprises a benzidine derivative represented by general formula (1) and molybdenum oxide,

(1)

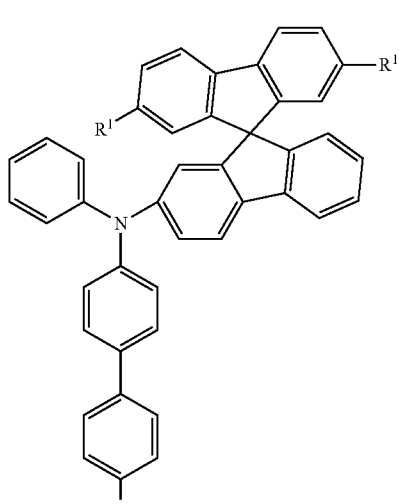

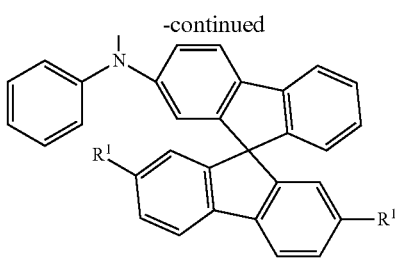

wherein R$^1$ represents hydrogen or an alkyl group having 1 to 4 carbon atoms, and
wherein the benzidine derivative and the molybdenum oxide are mixed in the first layer.
2. A light-emitting element comprising:
a pair of electrodes; and
a first layer formed between the pair of electrodes,
wherein the first layer comprises a benzidine derivative represented by formula (2) and molybdenum oxide, and (2)

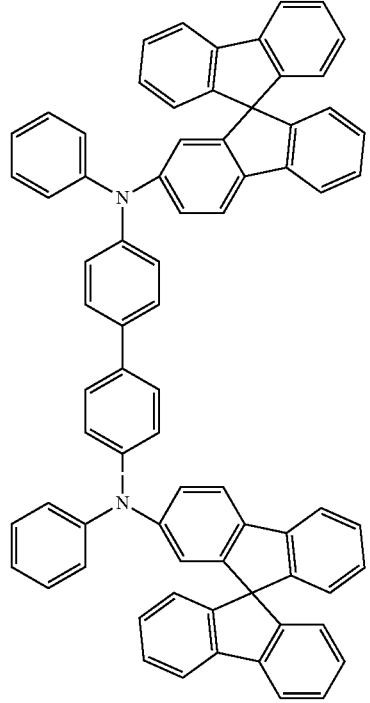

wherein the benzidine derivative and the molybdenum oxide are mixed in the first layer.
3. The light-emitting element according to any one of claims 1 and 2, further comprising a second layer between the pair of electrodes,
wherein the first layer is in contact with one of the pair of electrodes,
wherein the second layer is provided between the first layer and the other one of the pair of electrodes, and
wherein the second layer comprises the benzidine derivative.
4. A light-emitting device comprising:
a semiconductor film including an impurity region;
a first electrode connected to the impurity region;
a second electrode opposed to the first electrode; and
a first layer, provided between the first electrode and the second electrode, wherein the first layer comprises a benzidine derivative represented by general formula (1) and molybdenum oxide,

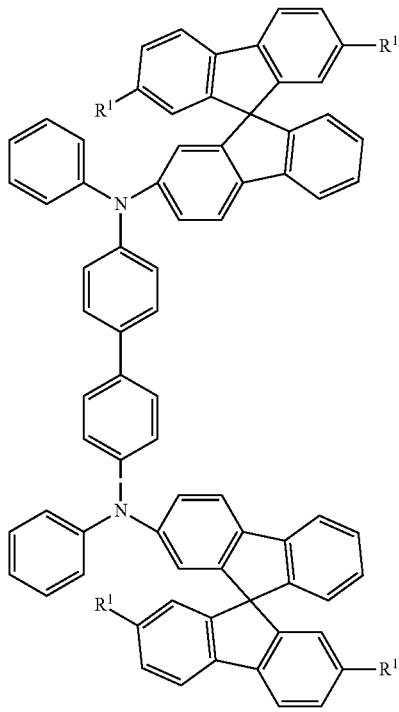

(1)

wherein $R^1$ represents hydrogen or an alkyl group having 1 to 4 carbon atoms, and wherein the benzidine derivative and the molybdenum oxide are mixed in the first layer.

5. A light-emitting device comprising:

a semiconductor film including an impurity region;

a first electrode connected to the impurity region;

a second electrode opposed to the first electrode; and a first layer provided between the first electrode and the second electrode, wherein the first layer comprises a benzidine derivative represented by formula (2) and molybdenum oxide, and

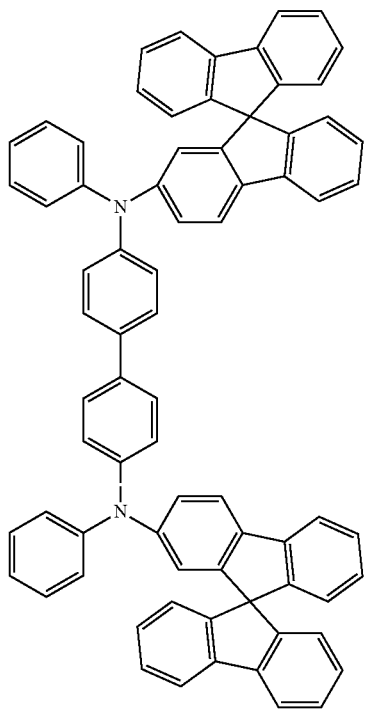

(2)

wherein the benzidine derivative and the molybdenum oxide are mixed in the first layer.

6. The light-emitting device according to any one of claims 4 and 5, further comprising a second layer between the first layer and the second electrode, wherein the first layer is in contact with the first electrode, and wherein the second layer comprises the benzidine derivative.

7. The light-emitting element according to any of claims 1 and 2, wherein the first layer further comprises rubrene.

8. The light-emitting device according to any of claims 4 and 5, wherein the first layer further comprises rubrene.

* * * * *